US010416051B2

(12) United States Patent
Poulsen et al.

(10) Patent No.: US 10,416,051 B2
(45) Date of Patent: Sep. 17, 2019

(54) TISSUE PROCESSING APPARATUS

(71) Applicant: Dako Denmark A/S, Glostrup (DK)

(72) Inventors: Tim Svenstrup Poulsen, Horsholm (DK); Steen Hauge Matthiesen, Hillerod (DK)

(73) Assignee: DAKO DENMARK A/S, Glostrup (DK)

( * ) Notice: Subject to any disclaimer, the term of this patent is extended or adjusted under 35 U.S.C. 154(b) by 0 days.

(21) Appl. No.: 16/007,756

(22) Filed: Jun. 13, 2018

(65) Prior Publication Data

US 2018/0306686 A1 Oct. 25, 2018

Related U.S. Application Data

(63) Continuation of application No. 14/883,257, filed on Oct. 14, 2015, now Pat. No. 10,031,052, which is a
(Continued)

(51) Int. Cl.
*G01N 1/00* (2006.01)
*G01N 1/28* (2006.01)
(Continued)

(52) U.S. Cl.
CPC .............. *G01N 1/2813* (2013.01); *G01N 1/30* (2013.01); *G01N 1/312* (2013.01)

(58) Field of Classification Search
CPC ........................................................ G01N 1/00
See application file for complete search history.

(56) References Cited

U.S. PATENT DOCUMENTS 4,061,108 A 12/1977 Levine et al.
5,409,832 A 4/1995 Pocock
(Continued)

FOREIGN PATENT DOCUMENTS

AU 2008335997 A1 6/2009
EP 357625 A1 3/1990
(Continued)

OTHER PUBLICATIONS

"Horizontal plane", https://en.wikipedia.org/wiki/Horizontal_plane, printed Jul. 6, 2016, 2 pages.
(Continued)

*Primary Examiner* — Jyoti Nagpaul

(57) ABSTRACT

An apparatus (100) for processing a biological sample (101). The biological sample being arranged on a first planar surface (102) of a carrier (103). The apparatus comprises a second planar surface (104) arranged substantially parallel to said first planar surface and at a first distance from said first planar surface, said first planar surface and said second planar surface are arranged at an angle (A) greater than zero degree from the horizontal plane (HP); supply means (126, 131, 220) for supplying an amount (105) of a liquid that is to be applied to said biological sample. The first planar surface and second planar surface are configured to be arranged at a second distance from each other, said second distance being such that said supplied amount of liquid is distributed over said biological sample when said first planar surface and said second planar surface are brought to said second distance from each other.

23 Claims, 17 Drawing Sheets

Related U.S. Application Data continuation of application No. 14/503,925, filed on Oct. 1, 2014, now Pat. No. 9,182,323, which is a continuation of application No. 12/747,023, filed as application No. PCT/DK2008/000430 on Dec. 9, 2008, now Pat. No. 8,877,144.

(60) Provisional application No. 61/012,481, filed on Dec. 10, 2007.

(51) Int. Cl.
*G01N 1/31* (2006.01)
*G01N 1/30* (2006.01)

(56) References Cited

U.S. PATENT DOCUMENTS

| | | |
|---|---|---|
| 5,451,500 A | 9/1995 | Stapleton |
| 5,958,760 A | 9/1999 | Freeman |
| 6,319,470 B1 | 11/2001 | Lefevre et al. |
| 8,315,445 B2 | 11/2012 | Sorenson et al. |
| 8,315,899 B2 | 11/2012 | Samuhel et al. |
| 8,758,707 B2 | 6/2014 | Watkins et al. |
| 2005/0025672 A1 | 2/2005 | Nakaya et al. |
| 2005/0270642 A1 | 12/2005 | McLellan et al. |
| 2006/0239858 A1 | 10/2006 | Becker |

FOREIGN PATENT DOCUMENTS

| | | |
|---|---|---|
| EP | 0357625 A1 | 3/1990 |
| EP | 357625 B1 | 1/1992 |
| EP | 0740142 A2 | 10/1996 |
| EP | 2235496 B1 | 10/2015 |
| EP | 2982960 | 2/2016 |
| WO | 8807679 | 3/1988 |
| WO | 2005066327 A1 | 7/2005 |
| WO | 2006116035 A2 | 11/2006 |
| WO | 2007122265 A1 | 11/2007 |

OTHER PUBLICATIONS

International Search Report dated Jun. 5, 2009, International Application No. PCT/DK2008/000430, 11 pages.
Extended European Search Report dated Feb. 1, 2019, Application No. 18198629.0, 11 pages.

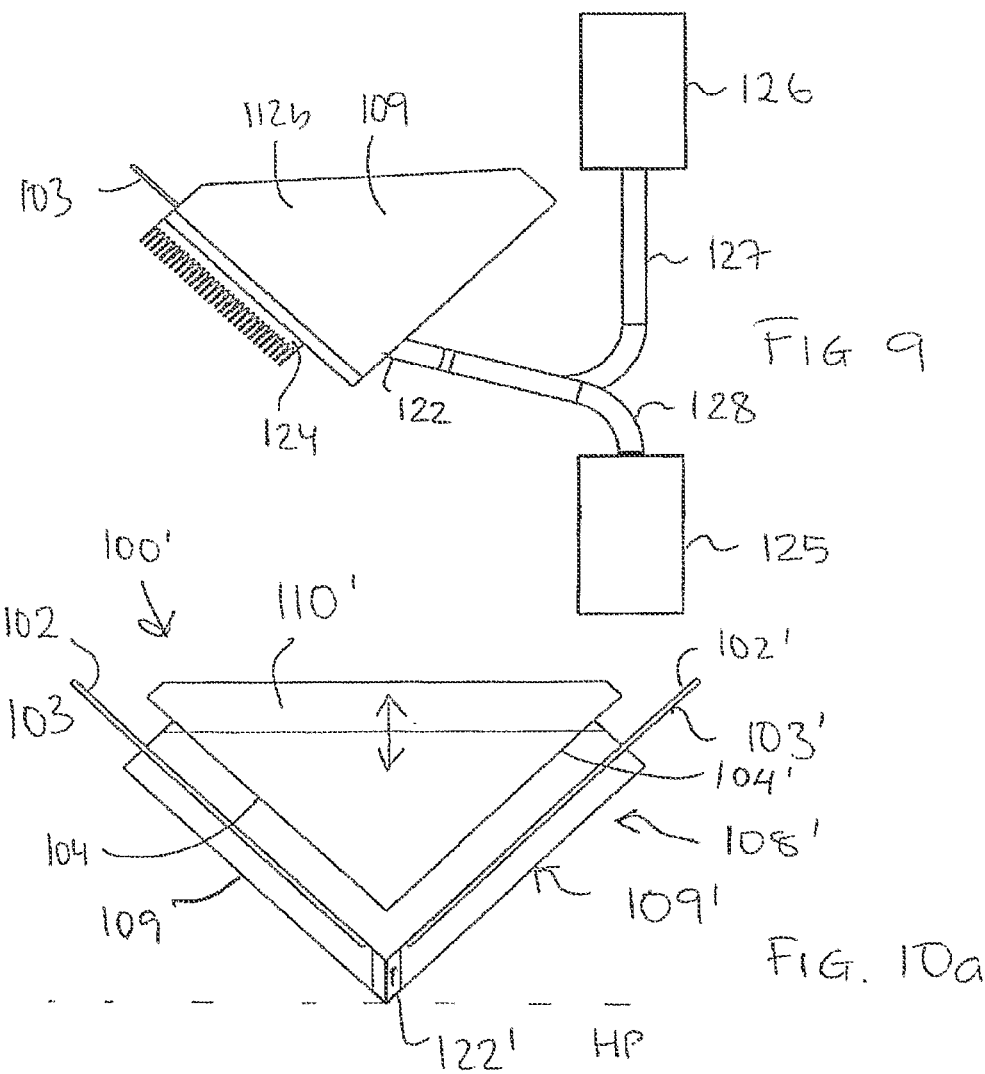

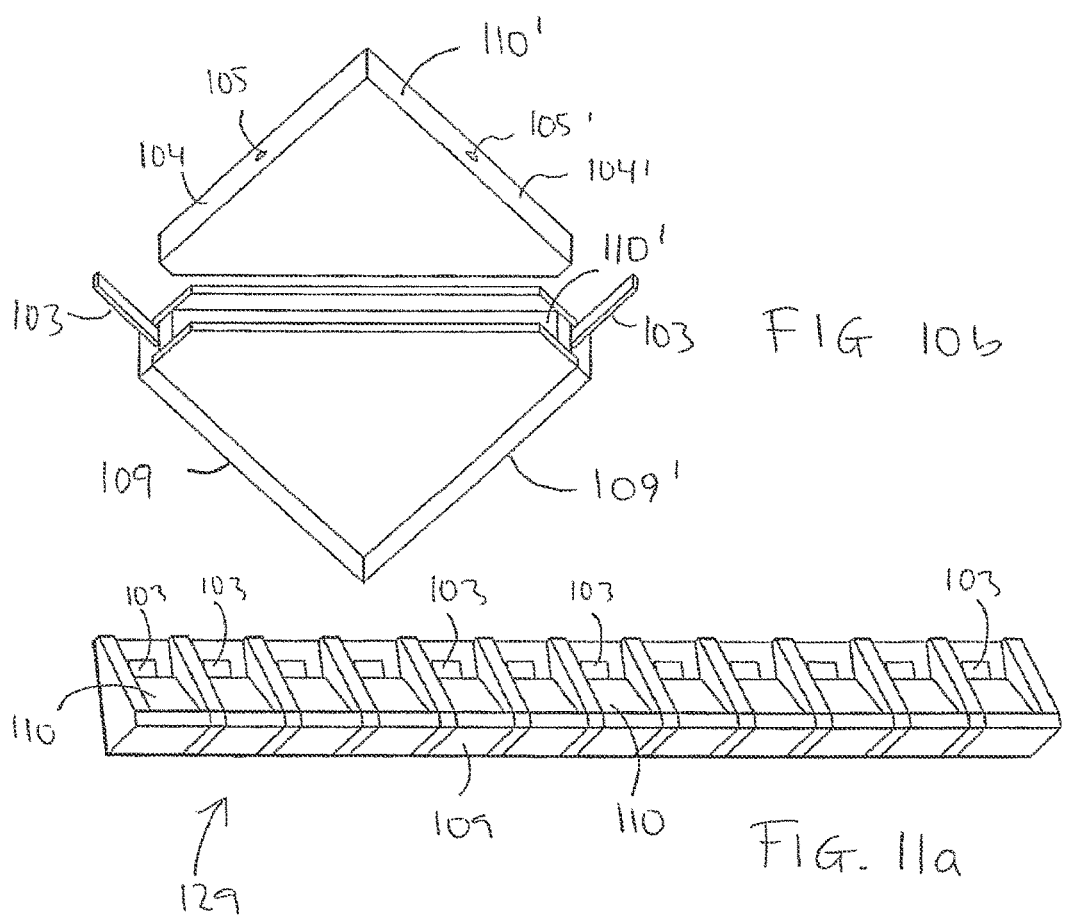

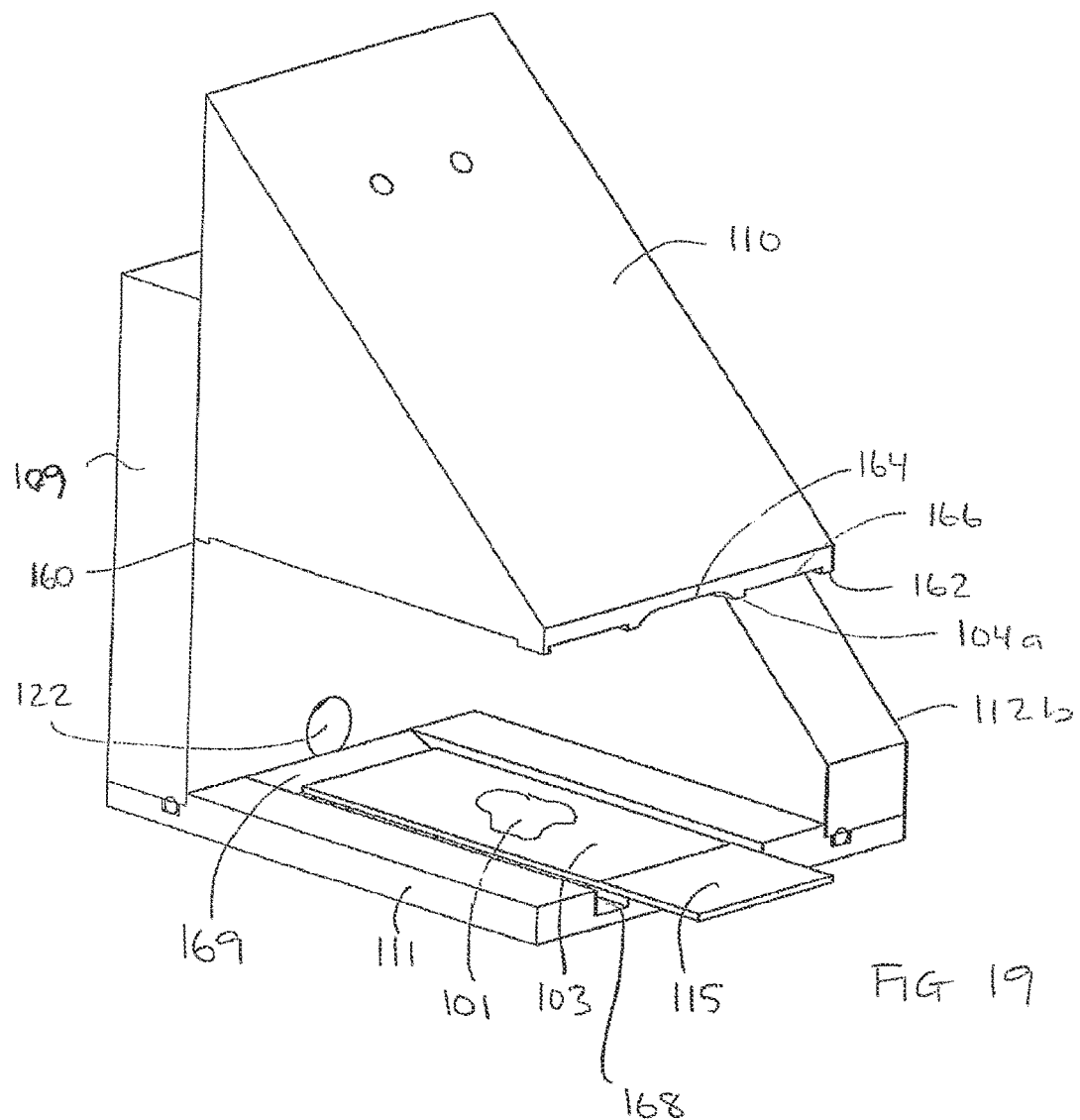

TISSUE PROCESSING APPARATUS

This is a continuation of U.S. patent application Ser. No. 14/883,257, filed Oct. 14, 2015 (published on Feb. 4, 2016 as Publication No. 2016/0033372), which is a continuation of U.S. patent application Ser. No. 14/503,925, filed Oct. 1, 2014 (issued on Nov. 10, 2015 as U.S. Pat. No. 9,182,323), which is a continuation of U.S. patent application Ser. No. 12/747,023, filed Sep. 3, 2010 (issued on Nov. 4, 2014 as U.S. Pat. No. 8,877,144), which is a U.S. National Phase Patent Application based on PCT/DK2008/000430, filed Dec. 9, 2008, which claims the benefit of U.S. Provisional Patent Application No. 61/012,481, filed Dec. 10, 2007, all of which are incorporated herein by reference in their entirety.

TECHNICAL FIELD

The present invention relates to processing of a biological sample for e.g. histological and cytological examination. Especially, the present invention relates to the processing of a biological sample, for example a thin tissue section, using a small quantity of a processing liquid.

BACKGROUND OF THE INVENTION

Sample processing in immunohistochemical ("IHC") applications, for example, and in other chemical and biological analyses may involve one or a number of various processing sequences or treatment protocols as part of an analysis of one or more samples. Typically, such treatment protocols are defined by organizations or individuals requesting analysis, such as pathologists or histologists attached to a hospital, and may be further defined by the dictates of a particular analysis to be performed.

A fluorescence In-situ hybridization (FISH) procedure is traditionally a two days manual procedure. Attempts have been made to automate parts of the procedure in order to shorten the processing procedure and to reduce the number of manual steps. For example, the first day pre-treatment procedure has been automated with an instrument VP2000™ (Vysis, Abbott Molecular), in which instrument a robot moves slides from one jar to another. However, the problem so far has been to combine the pre-treatment steps of the first day and the washing steps of the second day with the strict physical and environmental requirements of the denaturation and hybridization steps in between. In these steps it is preferred to use small volumes of processing liquids and provide a precise control of the humidity in the processing chamber surrounding the processed tissue section, and to provide controlled heating and cooling in order to obtain consistent FISH results.

Automated IHC and ISH staining instruments have been introduced by Ventana Medical Systems Inc. (BenchMark™ and Discovery™) and VisionBiosystem (Bond™). A drawback with these instruments is that they only provide a fixed processing volume, i.e. the processing chamber is of a fixed volume. The processing chamber volume in the instrument being at least 100 micro liters.

The BenchMark™ instrument, having a capacity to process 30 slides, needs to cover the tissue section to be processed and the applied processing liquid with oil in order to reduce evaporation of the processing liquid. If not covered by oil, the evaporation of processing liquid will deteriorate the processing result.

The Bond™ instrument, having a capacity to process 30 slides, has a small processing chamber which is clamped over each tissue section and each carrier. By clamping the processing chamber over each carrier, an individual staining cavity is created.

Some of the drawbacks with prior art instruments are that they require relatively large volumes, about 150-200 micro liters, of processing liquid, that they do not provide as good results as manual processing, and that they do not provide a variable volume of processing liquid to be used by providing a processing chamber having a variable volume.

An aim of the present invention is to solve these and other problems and drawbacks with the prior art system.

For example, an object of the present invention is to provide processing of a biological sample arranged on a carrier using a small quantity of processing liquid.

Another object of the present invention is to provide processing of a biological sample arranged on a non-horizontal carrier.

Yet another object of the present invention is to provide a processing apparatus for processing of a biological sample arranged on a carrier, the processing apparatus being configured to provide a variable volume for processing liquid.

Another object is to provide automated processing of a biological sample arranged on a carrier using a small quantity of processing liquid.

SUMMARY OF THE INVENTION

The present invention concerns molecular pathology, i.e. the examination at a molecular level of the DNA; mRNA, and proteins that cause or are otherwise associated with disease. The present invention relates to processing of a biological sample for e.g. histological and cytological examination. Especially the present invention relates to the processing of a thin biological sample, e.g. a tissue section, using a small quantity of a processing liquid.

In particular, the invention relates to processing, treating and/or staining of at least one biological sample, e.g. a tissue section, accommodated on a carrier as well as to the control of the humidity and temperature during the processing and/or treating and/or staining.

It should be understood that the present invention may be used in the fields of cytology and histology, molecular biology, biochemistry, immunology, microbiology, and cell biology. In particular, the invention relates to the fields of molecular cytogenetics and immunohistochemistry, for processing biological samples in immunohistochemistry (IHC), in-situ hybridization (ISH), fluorescent in-situ hybridization (FISH), chromogenic in-situ hybridization (CISH), special stains (SS), silver in-situ hybridization (SISH), microarrays (tissue, protein, RNA, DNA, PNA, LNA, etc.) as well as other chemical and/or biological applications.

The inventive processing apparatus provides a variable processing volume, whereby different biological samples can be processed using different volumes of processing liquids, e.g. different volumes of reagent can be used for different biological samples.

Advantages of Embodiments of the Present Invention

Embodiments of the present invention comprise one or more of the following features:

| Feature | Advantages | Explanations/Comment | |
|---|---|---|---|
| Angle A (different from horizontal) | passive draining | gravity | |
| | physical container variable volume | Contained liquid Different volumes of processing liquid may be used | An angle and gravidity combined can be used to hold liquid contained in "open chamber" system |
| | smaller footprint of apparatus | Compared to horizontal slide position | |
| | Faster drying | Liquid dries faster by running down a slide with an angle during drying during heating | |
| | No coffee ring effect | Due to the angle | |
| | Minimize air bubbles | Air can easier move away due to angle | |
| | Minimize evaporation | The higher angle combined with the blocks area reduces the surface of which evaporation can occur | |
| | liquid/humidity reservoir | An angle can by gravity hold liquid for humidity control separated from reagents in a simple manner | |
| Geometry of block | Round shaped piston | The bottom of a piston can be shaped such that it fits to a slide. It can also cover a portion of a slide or the whole slide | |
| | Two sided block to two slides or more | Notice that the angle of which the block lowered to the slide is not perpendicular as the one slide block | |
| | Square | Cover a portion of slide or cover whole slide | |
| | Rectangular | Cover a portion of slide or cover whole slide | |
| | Diamante | As batch and/or single mode | |
| | Block(s) system geometry | They can e.g. be placed in carousel, linear, spiral etc.. | |
| Block | Variable volume | Provide a span of a minimum factor or 1000 in volume, e.g. from 20 micro litres to 20 millilitres, or even more | |
| | Spread of reagent | Bottom can be flat or modified to fit as a "cover glass" for e.g. a portion of the slide surface area | |
| | Controlled different volumes | By moving block in one dimensional direction volumes can vary from e.g. 10 micro litres to 100 millilitres | |
| | Efficient mixing | Increase kinetic speed, mix different reagents under/on/above/slide | |
| | no cover glass | Block con also contain the function of a traditional cover glass | |
| | no cover glass sealant batch mode | One block made such that it covers multiple slides, e.g. 12 | |
| | single mode | One block made such that it covers one slide | |
| | "Humidity" reservoir | For example in block and/or in chamber | |
| | fast multi processing Simple design Slide position | block or platen or both | |
| | Controlled environment (humidity/temp) No oil or equivalent for | | |

-continued

| Feature | Advantages | Explanations/Comment | |
|---|---|---|---|
| | sealing necessary | | |
| | Fast temperature ramping due to small volumes | | |
| | Many possibilities for reagent addition | above, through wall side, through platen, capillary forces, through block, out side block (pulling slide out) | |
| | Liquid reservoir | Can be build into block, wall or platen | |
| | Semi closed changed to open container by removing the block | | |
| | The block can move by one dimension movements | | |
| | Automated movement of block | Easily automated | |
| | Nose barrier | Might have a form for O-ring to assist sealing (so far not required) | |
| | One brick can in principle perform all types of processes. However, it might be preferred to optimize the block to different types of processes such as e.g. IHC and FISH especially in light of the potential long hybridisation time (14-20 h). | | |
| | Made of a poor heat conductor | Fast ramp times of small liquid volumes | |
| Slide position | In platen (bottom plate) | Below surface, at surface or above surface of platen | |
| | In block | Below surface, at surface or above surface of platen | |
| | Slide facing down | Reagent e.g. through platen can be pre-heated by platen | |
| | Two slides at same time (same reagent e.g. Her2) | Use less reagent, smaller instrument | |
| | Slide may be "tilted" | X, Y, Z dimension | |
| | All steps while slide is in one position | Capable of performing all reagent processing steps | |
| | Variable volume in batch mode | Batch instrument | |
| | ISH, FISH, CISH, SISH, SS, IHC etc | | |
| | Combined batch and single mode | Block can be designed to do both | By e.g. building in a small wall, going into the block, between the slide positions both batch and single mode can be combined |
| | Multi flexible system | Can potentially run with or without a rack holding the slides | |
| Mixing | In chamber by moving block e.g. 1 mm up and down | | |
| | Built in reagent mixing station in chamber | | |
| | Increased reaction speed on slide with active mixing and temperature control | | |
| | Mix concentrate of e.g. Ab to RTU on side, of diverse buffer concentrate to RTU etc. (RTU = Ready-to-use liquid) | | |
| | Mixing during incubation | Can potential decrease incubation times and make it possible to use smaller volumes than a static incubation. | |
| | Mixing large and small volumes | By moving the brick a very efficient mixing can be made. | By having an angle there will be no "dead" spot on mixing of small volumes |

-continued

| Feature | Advantages | Explanations/Comment | |
|---|---|---|---|
| | | | as gravity together with capillary forces see to that the liquid will move to the bottom part of the slide and thereby secures a homogenous mixing (and washing) in contrast to horizontal. |
| | Large wash volumes e.g. 4 mL | The whole chamber is in use | Movement of brick will increase wash effiency |
| | Small wash volumes e.g. 150 uL | "Coverslide" of brick is in use | Small movement of brick will increase wash efficiency |
| | Circulation of liquid | Circulation of liquid can e.g. be performed by outlet through overflow drain and back again through the bottom inlet. | |
| Reagent inlet/outlet | Assist release of slide after e.g, o/n hybridization by inlet of wash buffer through bottom before raising block Possibility of small volumes with semi-closed (read closed) block position Inlet channel through chamber wall | | |
| Chamber | Overflow drain | Can be used to e.g. separate organic waste, it secure against overflow, used in washing steps etc. | |
| | Inlet | | |
| | Outlet | | |
| | Guide rail for block | | |
| | Chamber sealant, e.g. by o-rings | Around chamber and/or block | Secure tree movement with potential material expansion or contraction at diverse temperatures |
| | Reservoir for liquid to secure high relative humidity | | |

An embodiment includes an apparatus for processing a biological sample, said biological sample being arranged on a first planar surface of a carrier, said apparatus comprising:
 a second planar surface at a first distance from said first planar surface, said first planar surface is arranged at an angle (A) greater than zero degree from the horizontal plane (HP);
 a liquid supply for supplying an amount of a liquid that is to be applied to said biological sample;
 wherein said first planar surface and said second planar surface are configured to be arranged substantially parallel at a second distance from each other, said second distance being different from said first distance and being such that said supplied amount of liquid is distributed over said biological sample when said first planar surface and said second planar surface are brought to said second distance from each other.

In an embodiment the second planar surface is arranged substantially parallel to said first planar surface and at a first distance from said first planar surface, said first planar surface and said second planar surface are arranged at an angle (A) greater than zero degree from the horizontal plane (HP).

A simple construction is needed to move the second planar surface from the first position to the second position when the first and second surfaces are parallel in both positions.

In embodiments, the sample carrier is arranged at an angle A from the horizontal plane, whereby passive draining of liquid from the sample is provided. The passive draining is due to gravity and/or capillary forces. An advantage by such an arrangement is that during drying/dehydration/baking of specimen, liquid is removed faster due to the combined effect of the heating and the passive draining than compared with sample processing apparatuses having sample carriers arranged parallel to the horizontal plane.

Arranging the sample carrier at an angle A also provides that different volumes of processing liquid may be used. The liquid can be held in a capillary field when using small volume and when using larger volume the chamber walls and block act as a chamber and retain the liquid. Such a processing chamber can suitably function as a humidity chamber.

Yet another advantage with providing the sample carrier at an angle A is that a smaller footprint of the apparatus may be achieved than if the sample carrier was arranged parallel with the horizontal plane.

Another advantage is that air bubbles trapped in the processing liquid between the sample carrier and the block more easily may escape From the processing liquid than if the sample carrier was arranged parallel to the horizontal plane.

Yet another advantage is that the angle A in combination with the area of the block reduces the surface from which evaporation can occur, whereby smaller volumes of processing liquid may be used than if the evaporation surface was larger.

A further advantage is that the angle A and the gravity can hold liquid for humidity control separated from reagents and specimen in a simple manner by draining condensed liquid back to a humidity reservoir. Thereby, the risk of mixing the reagent used in the specimen processing with the liquid used for humidity control is reduced.

In embodiments of the invention, the block may be configured as a round Shaped piston. The bottom of the piston may be shaped such that it fits to a sample arranged on sample carrier. The bottom of the piston may be designed to Cover a portion of a sample carrier or the whole sample carrier.

In embodiments, the block is a two-sided block each of which side is configured to fit to a sample carrier, whereby two samples potentially can be processed simultaneously.

In embodiments having a block with e.g. a square or rectangular shape, the block should be designed to cover a portion of the sample carrier or to cover the entire sample carrier. Embodiments with a diamante shaped block provides for batch and/or single mode operation.

However, it should be understood that the block may have another suitable design and dimension than those described herein.

Embodiments of the invention may also comprise one or more blocks arranged in a carousel arrangement, a linear arrangement, or spiral arrangement etc. In some embodiments one or more of the arrangements can be stacked.

An advantage with the use of a block is that a variable processing volume can be provided. It is for example possible to provide a span of a minimum factor of 1000 in volume, e.g. from 20 micro liters to 20 milliliters, or even more. Further, by moving block in e.g. a one-dimensional direction, the processing volume can vary from e.g. 10 micro liters to 100 milliliters. Furthermore, by means of the block, the processing liquid, e.g. reagents, can be spread over the sample to be processed. The bottom of the block can be flat or modified to fit as a "cover glass" over e.g. a portion of the sample carrier surface area.

Yet another advantage with a movable block is that an efficient mixing of processing fluids can be provided by moving the block and thereby providing a mixing movement in the fluids.

Yet another advantage with the block is that no cover glass may be needed, the block can also contain the function of a traditional cover glass. A further advantage with the block of the present invention is that no cover glass sealant is required. Further, depending of the design of the block, samples can be processed in batch mode by a block covering multiple samples or in single mode by a block covering a single sample only. Another advantage is that the block can be configured to comprise a humidity reservoir, whereby a desired relative humidity may be provided at the sample to be processed. The humidity reservoir can also be placed in the platen.

In embodiments, the block provides a controlled environment, i.e. a controlled humidity and/or a controlled temperature.

In embodiments, no oil or equivalent for sealing may be necessary.

Embodiments of the invention provide a fast temperature ramping due to small volumes of the processing liquids used.

Embodiments of the invention may also provide different possibilities for reagent supply. The reagent may for example be supplied from above, through the wall side, through the platen, by means of capillary forces, through the block, from the outside of the block by pulling the slide out from the apparatus, etc.

Embodiments of the invention may also provide a liquid reservoir, which may be arranged at the block, the wall or the platen (the bottom plate of the processing chamber).

In embodiments, the processing apparatus is configured with a semi closed chamber being a closed chamber when the block is in a processing position.

In embodiments, the block may be moved by one-dimensional movements.

In embodiments, the block may be moved by two-dimensional movements.

Some embodiments provide automated movement of the block.

In embodiments, the apparatus and the block may be configured to perform all types of sample processing. However, it might be preferred to optimize the block to different types of sample processing, such as e.g. IHC and ISH, or processing steps, such as baking, target retrieval, deparaffination, stringency wash, cover slipping, staining, enzymatic treatment, etc. In the context of the present invention the sample processing is to be understood as the active process of qualifying or quantifying the presence of a specific compound.

In embodiments, the block is configured of a poor heat conducting material, whereby the block does not or to a limited extent conduct heat supplied to the processing liquid. Thus, the temperature of the processing liquid may be changed quickly within a short ramp time.

In embodiments of the present invention, the sample may be arranged at the bottom plate of the processing chamber. Further, the sample may be arranged below the surface of, at the surface of or above the surface of the bottom plate.

In other embodiments, the sample is arranged at the block. Further, the sample may be arranged below the surface of, at the surface or above the surface of the block.

In some embodiments, the sample on the carrier is facing down, i.e. the sample is arranged at the block facing the bottom plate of the processing chamber, whereby processing liquid, e.g. a reagent, supplied through the bottom plate can be pre-heated by the bottom plate without the sample being pre-heated by the bottom plate.

in some embodiments, two slides are processed at the same time using the same processing liquid, e.g. a Her2 reagent, whereby less processing liquid may be used than if the samples were processed sequentially.

Further, the sample carrier may be arranged in a "tilted" position, e.g. the sample carrier may be titled in the X, Y, or Z direction. If the sample carrier is arranged at an angle A from the horizontal plane, the footprint of the apparatus may be less than if the sample carrier was arranged parallel with the horizontal plane.

In embodiments, all processing steps are accomplished while the sample carrier is in one position.

In embodiments of the invention, one or more sample carriers are arranged in a rack, whereby the one or more sample carriers are handled by means of the rack, i.e. the one or more sample carriers may be inserted in or removed from the sample processing apparatus by inserting or removing the rack in or from the processing apparatus.

In embodiments of the invention, mixing is provided, in the processing chamber by moving the block e.g. about 1 mm up and down. Embodiments may also comprise a built in mixing station for processing liquid, e.g. a reagent mixing station in the apparatus, e.g. in the processing chamber. By means of active mixing and possible temperature control, an increased reaction speed on the sample is provided.

Embodiments may comprise mixing of concentrates e.g. antibodies (Ab) to ready-to-use reagents (RTU) on site or mixing of different buffer concentrates to RTU liquids, etc.

Embodiments may provide mixing during incubation, hereby incubation times may be decreased and smaller volumes of processing liquids, e.g. reagents, may be used as compared to the case of static incubation.

Embodiments may provide mixing of large and small liquid volumes. By moving the block, e.g. up and down, a very efficient mixing can be made. By having the sample carrier arranged at an angle to the horizontal plane there will be no "dead" spot when mixing small volumes since gravity together with capillary forces provide that the liquid will move to the bottom part of the sample carrier and thereby secure a homogenous mixing (and washing) in contrast to the case when the sample carrier is arranged parallel to the horizontal plane.

Embodiments of the invention providing mover lent of the block may also provide an efficient washing.

In embodiments of the invention, processing liquid is circulated through the processing chamber. For example, circulation of liquid may be performed by circulating the liquid out of a chamber outlet e.g. through an overflow drain and back again through an inlet, e.g. a bottom inlet, of the processing chamber.

In embodiments, the invention can be used to create a capillary field. For example the filling of the chamber/barrier partly or fully with liquid with the block in a first position, followed by moving the block to a second position creates capillary field when removing the non-capillary bound liquid from the chamber by e.g. a reagent outlet. Another way is to purge liquid through the chamber when the block is in the second position, creating a capillary field.

In embodiments, the processing chamber is provided With an overflow drain that may be used to e.g. separate organic waste, secure against overflow, used in washing steps etc. The processing chamber may also be provided with an inlet and an outlet. Further, in embodiments, the chamber may be provided with a guide rail for the block, in embodiments, the chamber may be provided with a chamber sealant, e.g. one or more o-rings. The chamber sealant may be arranged around the chamber and/or the block. In embodiments, secure free movement of the block taking potential material expansion Or contraction at diverse temperatures into consideration is provided.

In embodiments, the processing chamber comprises a reservoir for liquid to secure high relative humidity within the processing chamber.

In embodiments, the block may be designed to provide both a batch mode and a single mode of operation. For example, in such embodiments, the block may be provided with one or more protrusions, e.g. parallel wall sections, separating one or more sample carriers from each other when the block is arranged in a processing position.

Further embodiments include:

an apparatus wherein said supply means is configured to supply said amount of said liquid to a first part of said biological sample when said second planar surface is at said first distance from said first planar surface, and wherein said applied amount of liquid is distributed over a second part of said biological sample when said first planar surface and said second planar surface are brought to said second distance from each other, said second part of said biological sample having a larger surface area than said first part of said biological sample.

an apparatus wherein said supply means is configured to supply said amount of said liquid to said first planar surface or to a first part of said biological sample when said second planar surface is at said, second distance from said first planar surface, and wherein said applied amount of liquid is distributed over said biological sample due to capillary action.

an apparatus wherein said supply Means is configured to supply said amount of said liquid to said second planar surface, and wherein said supplied amount of liquid is distributed over said biological sample when said first planar surface and said second planar surface are at said second distance from each other.

an apparatus comprising a processing chamber having a first structure configured as a container having a bottom plate and walls and a second structure configured as a block, wherein said block is dimensioned to fit the opening of the container. Such a processing chamber can suitably function as a humidity chamber.

an apparatus wherein said bottom plate of said first structure is configured to support said carrier having said first planar surface.

an apparatus wherein said second structure is shaped as a block having a surface constituting said second planar surface.

an apparatus wherein said first structure comprising said second planar surface.

an apparatus wherein said second structure is configured to hold said carrier having said first planar surface.

an apparatus wherein said second planar surface comprises a planar elevation arranged to cover at least a part of said biological sample when said second planar surface is at said second distance from said first planar surface.

an apparatus wherein said elevation has the shape of a cover glass.

an apparatus wherein a sealing is arranged at the outer boundary of said planar elevation, whereby said applied amount of liquid is retained within a space defined by said sealing, said planar elevation, and, said part of said biological sample.

an apparatus comprising a control unit configured to control the supply of from said supply means.

an apparatus comprising a distance changing means for changing the distance between said first planar surface of said carrier and said second planar surface.

an apparatus wherein said distance changing means is an automatic distance changing means for automatically changing the distance between said first planar surface of said carrier and said second planar surface.

an apparatus comprising a control unit configured to control said distance changing means.

an apparatus wherein said carrier having said first planar surface is a microscope slide.

an apparatus wherein said angle (A) is larger than 0 degrees and smaller than or equal to 90 degrees.

an apparatus wherein said angle (A) is between 30 degrees and $0 degrees, an apparatus wherein said angle (A) is approximately 45 degrees.

an apparatus wherein said liquid is a reagent or a buffer solution.

an apparatus comprising a lid configured to be arranged at said first structure to enclose said carrier and said second structure during processing of said biological sample arranged on said first planar surface.

an apparatus comprising a reservoir arranged at surface of said lid that faces said second structure, said reservoir being configured to control the humidity within the processing chamber during processing of said biological sample.

an apparatus wherein said reservoir is configured as an elongated reservoir comprising an absorbing material.

a processing chamber for processing a biological sample arranged on a first planar surface of a carrier, said processing chamber comprising:
 a second planar surface arranged substantially parallel to said first planar surface and at a first distance from said first planar surface, said first planar surface and said second planar surface are arranged at an angle (A) from a horizontal plane (HP) during processing of said biological sample.

One or more of the following methods and steps can be performed by using the apparatus of the invention:
 Baking of e.g. formaldehyde fixed paraffin embedded tissue
 No reformatting, i.e. the sample carriers need not to be moved between processing steps—same position
 Fixation
 Dehydration—e.g. by heat after wash/rinse with e.g. water or dehydration with ethanol
 Deparaffination
 Target retrieval/pre-treatment
 Wash steps—Static (add liquid, no movement of brick) Or dynamic (brick movement or liquid flow) and flush
 Digestive treatment—Controlled temperature with potential low volume and controlled environment (humidity) secure more standardized digestion
 Denaturation
 Hybridization
 Stringency wash
 Mounting and coverslipping
 H&E staining
 Special stains
 IHC staining
 ISH (in-situ-hybridization)
 Counter staining

BRIEF DESCRIPTION OF THE DRAWINGS

The objects, advantages and effects as well as features of the present invention will be more readily understood from the following detailed description of embodiments of the invention, when read together with the accompanying drawings, in which:

FIG. 9 schematically shows an embodiment of the processing apparatus according to the invention;

FIGS. 10a and 10b schematically show an embodiment of a processing apparatus for processing two biological samples arranged on two carriers;

FIGS. 11a-11c schematically show embodiments of multi-processing apparatuses for processing several biological samples arranged on several carriers;

FIG. 19 schematically shows an embodiment of an apparatus for processing a biological sample according to the invention, in the embodiment one of the side wall being removed;

DETAILED DESCRIPTION OF THE INVENTION

Figure 1A:
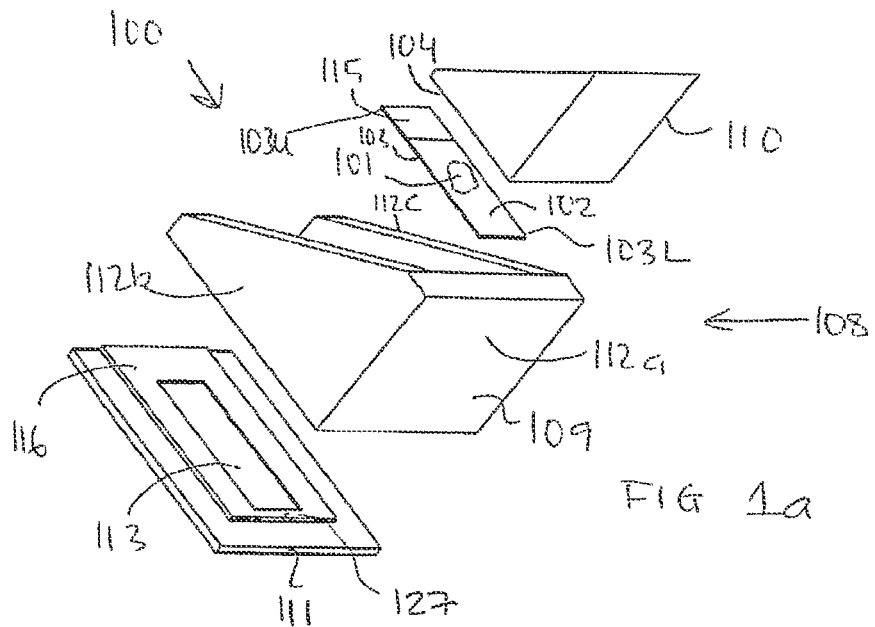
FIGS. 1a and 1b schematically show an embodiment of an apparatus for processing a biological sample according to the invention.

While the invention covers various modifications and alternative methods, apparatuses and systems, embodiments of the invention are shown in the drawings and will hereinafter be described in detail. However, it is to be understood that the specific description and drawings are not intended to limit the invention to the specific forms disclosed. On the contrary, the scope of the claimed invention is intended to include all modifications and alternative constructions thereof falling within the spirit and scope of the invention as expressed in the appended claims to the full range of their equivalents.

Figure 1B:
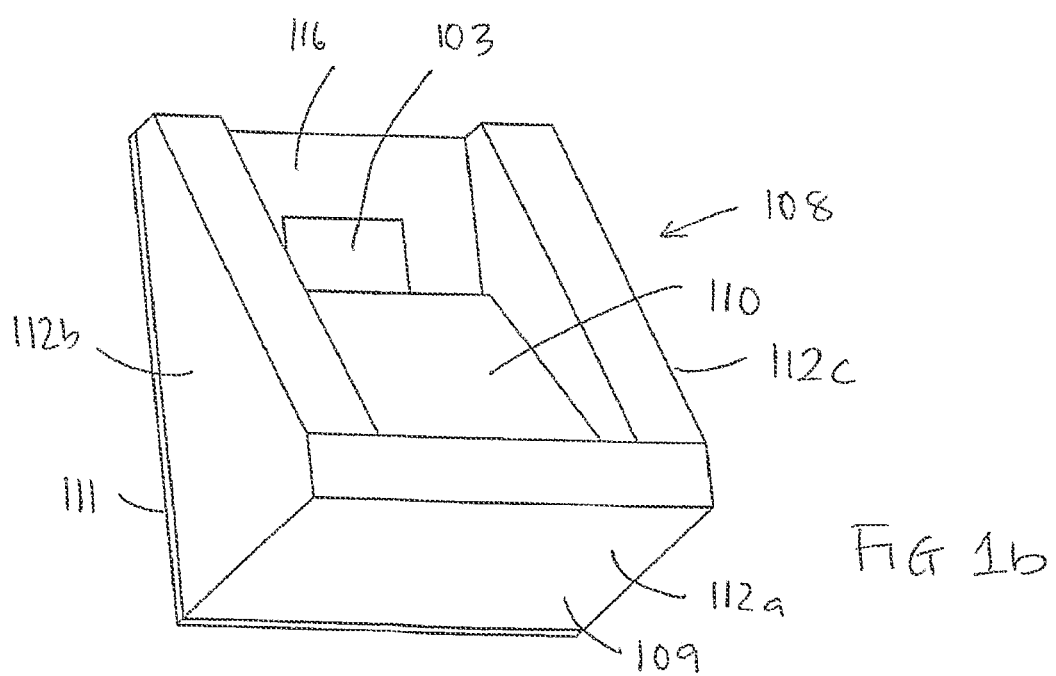

FIGS. 1a and 1b schematically illustrate an embodiment of an apparatus 100 for processing a biological sample 101 mounted on a first planar surface 102 of a carrier 103.

The biological sample 101 is preferably a thin tissue section of a tissue sample, e.g. a human tissue sample.

Figure 4:
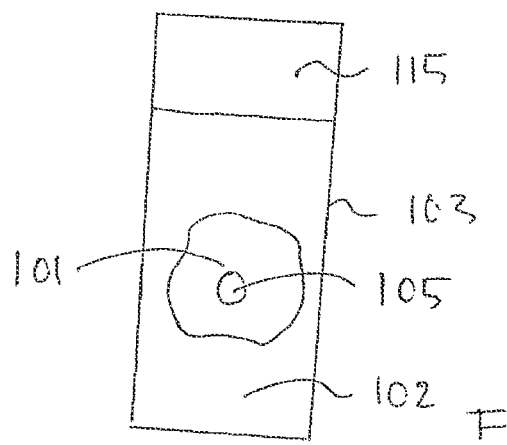
FIG. 4 schematically shows an embodiment of a carrier for a biological sample to be processed.

The carrier 103 may for example be a microscope slide 103 as illustrated in e.g. FIGS. 1a and 4, but it should be understood that the carrier may have another shape than rectangular. The carrier 103 comprises a first planar surface 102 carrying the biological sample 101. The carrier 103 comprises further an area 115 for information. For example the area 115 may be a read and/or write area for reading and/or writing information. The area 115 may for example carry an identification tag, such as a bar code label, identifying the biological sample 101. The area 115 may also carry information relating to the processing of the biological sample 101, which may be read by a reader (not shown) such as a bar code reader.

Figure 2:
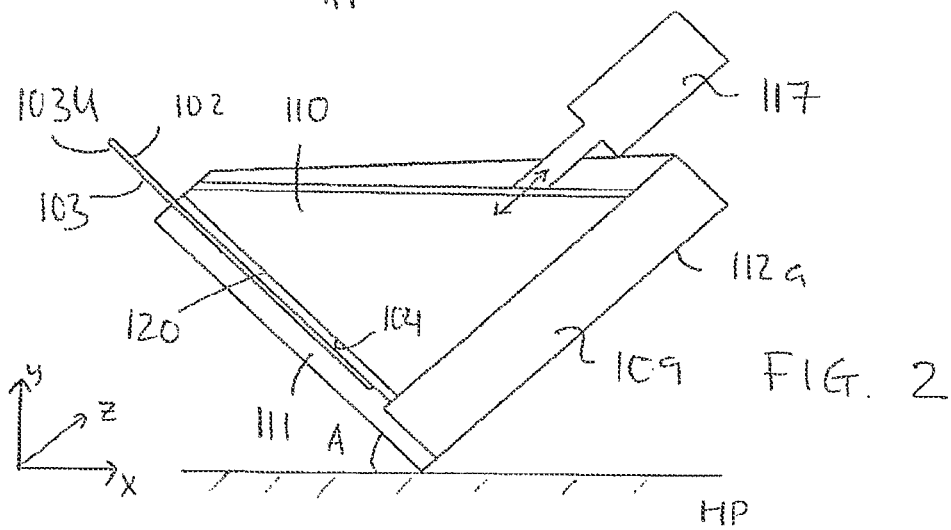
FIG. 2 schematically shows a cross-sectional view of an embodiment of an apparatus for processing a biological sample according to the invention.

The area 115 is preferably arranged at an upper part 103U of the carrier 103. The upper part 103U of the carrier 103 is an upper part of the carrier 103 when the carrier is in a tilted position, as illustrated in FIGS. 1 and 2. In this tilted position a lower part 103L of the carrier 103 is arranged in a lower part of the apparatus when the carrier is in the tilted position.

The carrier 103, a bottom plate 111 configured to support the carrier 103, and/or block 110 may comprise a groove (not shown) configured to fit a finger tip to ease the removal of the carrier after the processing procedure has finished.

Alternatively, a part of the carrier comprising the area 115 could protrude from the processing chamber as is shown in FIG. 2. In embodiments this part of the carrier protruding from the processing chamber may be removably attached to a carrier rack to ease removal of the carrier from the processing chamber and to facilitate further processing. In embodiments providing processing of multiple biological samples arranged on multiple carriers a multiple carrier rack is especially advantageous.

As illustrated in FIGS. 1a and 1b, the processing apparatus 100 comprises a processing chamber 108 comprising a first structure 109 and a second structure 110. The first structure 109 comprises a bottom plate 111 and side walls 112a, 112b, 112c, and the second structure 110 comprises a block 110.

In FIGS. 1a and 2, the first structure 109 and the second structure 110 are illustrated as having a triangular cross-section. However, it should be understood that this is only for illustrative purpose and that the first structure 109 and the second structure 110 may take other shapes, some of which shapes are shown in FIGS. 6a-6d. In some embodiments there is defined a small confined volume 120 at the biological sample 101 in order to provide minimal usage of process liquids.

In the embodiment shown in FIGS. 1a and 2, the confined volume 120 is defined by the biological sample 101 on the first planar surface 102 of the carrier 103, the inner sides of walls 112a, 112b, 112c, and by a second planar surface 104 of the block 110.

However, it should be understood that the confined volume 120 may be defined by the biological sample 101 on the first planar surface 102 of the carrier 103, the carrier 103 being mounted on the second structure 110 also called block, the inner sides of walls 112a, 112b, 112c, and the bottom plate 111.

Components and parts of the present invention defining the compartment having the confined volume 120 can be controlled with very high accuracy, whereby the biological sample 101 can be surrounded by a desired amount of liquid, e.g. processing liquid, during processing thereof.

FIG. 2 illustrates a cross-sectional view of an embodiment of the processing apparatus 100 when the block 110 is in a processing position, i.e. when the block 110 is in its lower-most position. This could also be explained as the block 110 is in a position where the distance between the biological sample 101 on the first planar surface 102 of the carrier 103 and the second planar surface 104 of the block 110 is as small as possible, i.e. the biological sample 101 is touching or almost touching the second planar surface 104 of the block 110.

As illustrated in FIGS. 1 and 2, the second planar surface 104 is arranged substantially parallel to said first planar surface 102. Further, the first planar surface 102 and the second planar surface 104 are arranged at an angle A from the horizontal plane HP. The angle A is preferably greater than zero degree, between 5 and 90 degrees, or more preferably between 30 and 90 degrees. In embodiments, the angle A is 45 degrees and in some embodiments the angle is about 20 degrees.

It should be understood that the angle A could be defined as greater than zero degree in the x, y, or z plane. Zero degree is defined as the angle A the carrier has to the horizontal plane (x plane) HP when the carrier is parallel to the horizontal plane HP.

Further, the angle A of the bottom plate and of the carrier provides a fast and easy removal of processing liquids. It should be understood that processing liquids may refer to all liquids applied to the biological sample and the carrier, such as washing solution(s), buffer(s), detection reagent(s), deparaffination reagent(s), special stain reagent(s), probe reagent(s), antibody reagent(s), etc. known to a person skilled in the art.

In embodiments of the invention, a seal e.g. a rubber seal such as an O-ring may be provided in order to seal the processing chamber.

As illustrated in FIGS. 6a-6d, the block 110 may have different shapes. For example, it may be rectangular, triangular, polygonal, convex, V-shape, \-shaped or diamond shaped. The block may be solid and it may be made of a combination of different materials.

In order to secure a high relative humidity within the processing chamber 106 during e.g. a hybridization step and thereby avoiding the biological sample 101 to be dried out, embodiments of the invention are configured to retain a small volume of liquid in the bottom of the processing chamber 108.

Figure 7:
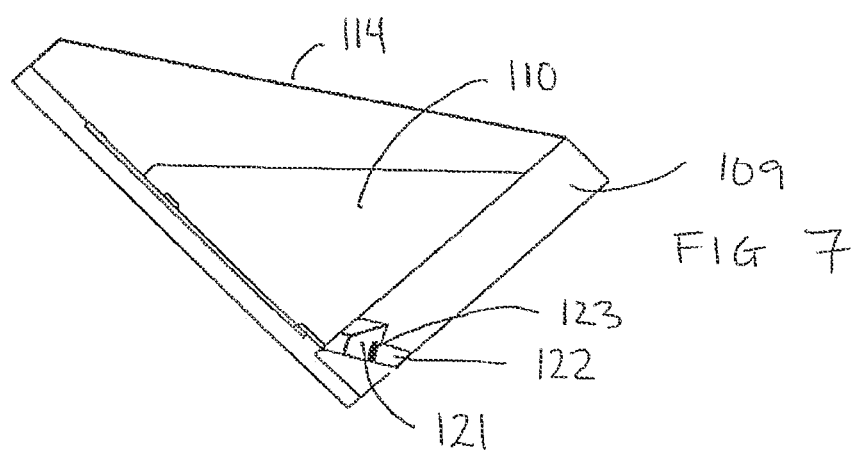
FIG. 7 schematically shows an embodiment of the processing apparatus according to the invention.
Figure 5A:
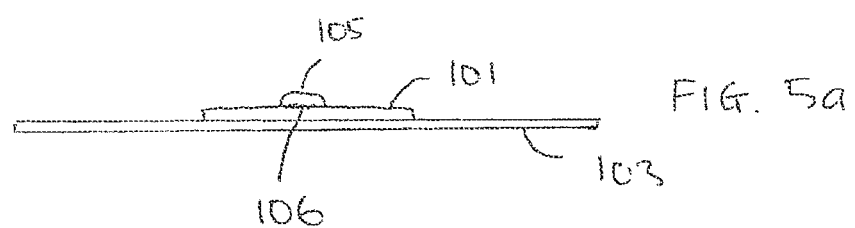
FIGS. 5a and 5b schematically show an embodiment of a carrier for a biological sample with an amount of a processing liquid applied.
Figure 5B:
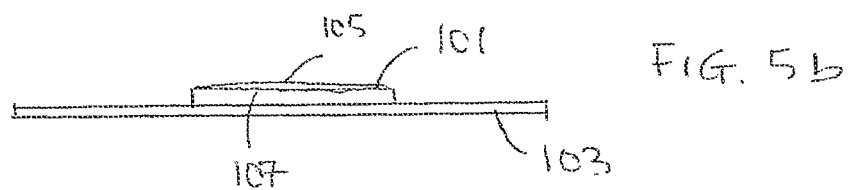

In embodiments, the apparatus 100 may be designed to provide a reservoir 121, i.e. a humidity chamber 121, for humidity control. The block 110 may comprise a recess (cf. FIGS. 14 and 16) in order to provide said reservoir 121. The reservoir can also be placed in the bottom plate or the was (cf. FIG. 7). The humidity chamber 121 is configured to control the relative humidity within the processing chamber 108 during processing of the biological sample 101.

The processing liquid may be removed from the bottom of the processing chamber 108 by means of an outlet, e.g. a drain 122, arranged in a bottom part. The drain 122 being controlled by means of a valve 123 e.g. a magnetic valve. When the magnetic valve is closed, the bottom of the processing chamber 108 is sealed. Draining of processing liquid may be accomplished by the gravitation force and/or capillary force acting on the processing liquid. This can be seen in FIG. 7.

In embodiments, the processing chamber 108 is provided with one or more pikes 127 in a bottom part thereof, e.g. at a liquid outlet. For example, the pikes 127 may be arranged in a bottom part of the block, cf. FIG. 14, and/or in the bottom plate 111, cf. FIG. 1. The pike 127 being configured to destroy and remove possible liquid bubbles occurring when the liquid is removed from the sample and the sample carrier.

In the embodiment shown in FIG. 1, the bottom plate 111 comprises a recess or a groove 113 for supporting the carrier 103. The recess 113 being designed to fit the dimensions of the carrier 103. However, it should be understood that the bottom plate 111 may comprise an elevation 116 comprising said recess 113. Further, it should be understood that the bottom plate 111 may support the carrier 103 without comprising a recess or a groove 113. Furthermore, the bottom plate 111 may comprise an elevation 116 for supporting the carrier 103.

Figure 8:
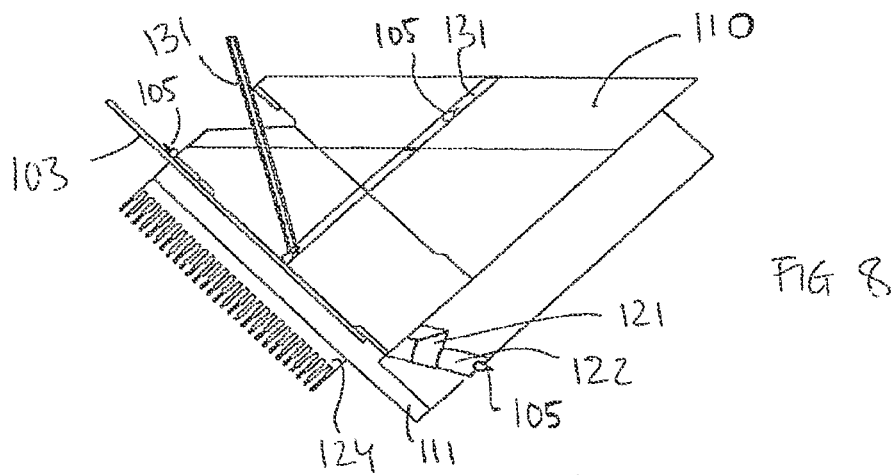
FIG. 8 schematically shows an embodiment of the processing apparatus according to the invention.
Figure 6A:
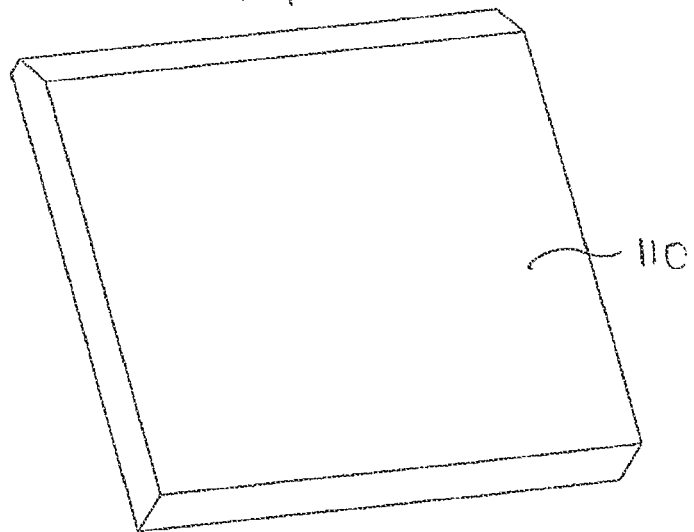
FIGS. 6a-6d schematically show different embodiments of a block for a processing apparatus according to the invention.
Figure 6B:
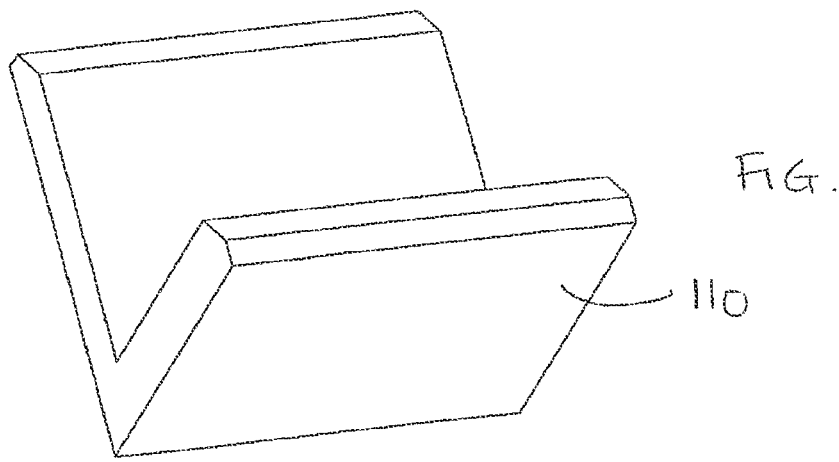
Figure 6C:
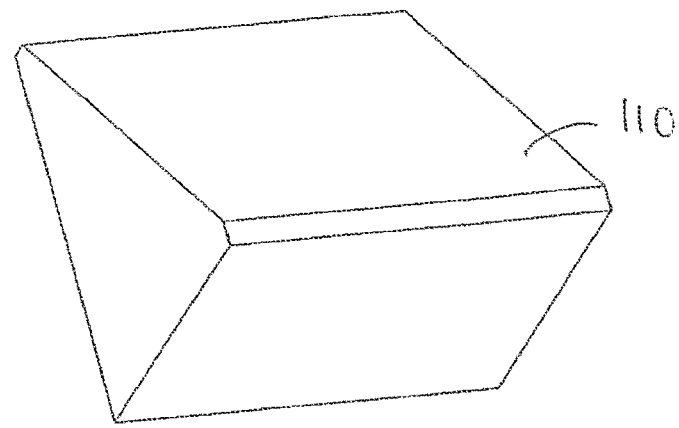
Figure 6D:
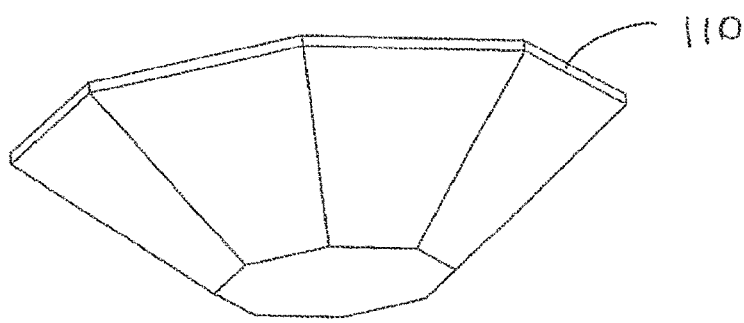

The bottom plate, sometimes also called platen, 111 should be of an efficient thermal conducting material when comprising a heating and/or cooling element(-s) 124, cf. FIG. 8. The temperature of the biological sample 101 on the carrier 103 may thereby be easily and efficiently controlled by either providing heating or cooling by means of a heating and/or a cooling element 124 arranged in the bottom plate 111.

In embodiments providing heating and/or cooling from the bottom plate 111, the block 110 may comprise an ineffective heat conducting material. The material may be Teflon™ coated to repel the applied processing liquid and to assist spreading out the applied processing liquid.

It should be understood that the heating and/or cooling element in embodiments may be arranged to supply heating and/or cooling from the biological sample facing side alone or in combination with the heating and/or cooling from the carrier facing side.

In embodiments providing heating and/or cooling from the biological sample facing side, the heating and/or cooling element may be arranged in the block.

In embodiments, the heating element 124 comprises heat wires or a Peltier element or a microwave element supplying in a controlled manner the heat required for the processing. In the ISH, IHC and special stains procedures of today, the temperature has to be varied considerably, e.g. between ambient temperature and 99 degrees Celsius.

In embodiments comprising a cooling element in e.g. the bottom plate 111, a channel (not shown) may be arranged in e.g. the bottom plate 111 to provide an efficient cooling of the carrier 103 and the biological sample 101 by ventilation by means of a fan (not shown). The fan may use the ambient air to cool the tissue section and carrier from a high temperature to a lower temperature. In embodiments, this may be done by letting ambient air pass cooling ribs (not shown) to cool down the bottom plate and thereby also the carrier 103, the tissue section 101 and the processing liquid applied. Similarly cooling can be performed by using water or a coolant instead of air. Due to the possibility of very small liquid volumes for liquids applied to the biological sample, fast temperature changes can be conducted.

FIGS. 8a, 8b, 8c, and 8d schematically show the supply of processing liquid to one or more samples according to embodiments of the inventive processing apparatus.

Figure 8A:
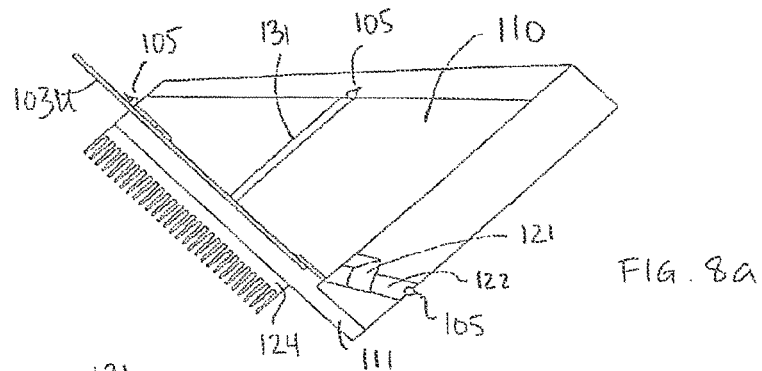
FIGS. 8a, 8b, 8c, and 8d schematically show how processing liquid may be supplied in embodiments of the processing apparatus according to the invention.

FIG. 8a shows that processing liquid, illustrated as a droplet 105, may be supplied by means of a supply means 131 arranged in the block 110, may be supplied at an upper part 103U of the sample carrier 103, and/or may be supplied by means of an inlet 122 arranged at the bottom part of the processing apparatus. Said inlet 122 can also function as a drain. According to embodiments, the block 110 is in a lower position, e.g. in a processing position, when the processing liquid is supplied.

Figure 8B:
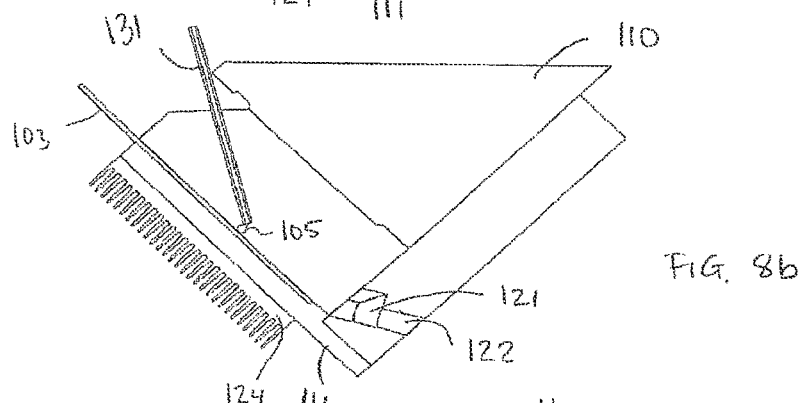

FIG. 8b shows that processing liquid may be supplied to the sample by means of a supply means 131 when the block 110 is in an upper position.

Figure 8C:
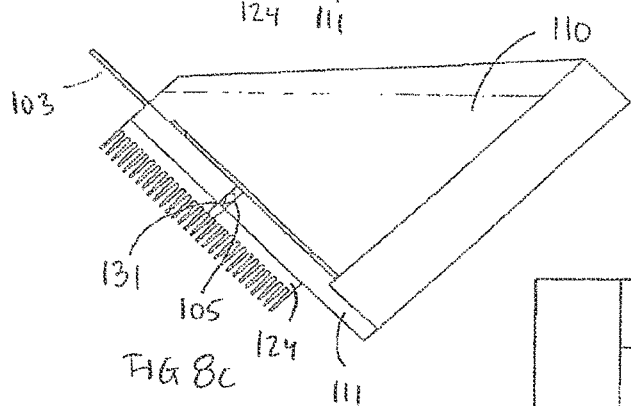

FIG. 8c shows an embodiment in which processing liquid is supplied by means of a supply means 131 arranged in the bottom plate 111 of the processing apparatus.

Figure 8D:
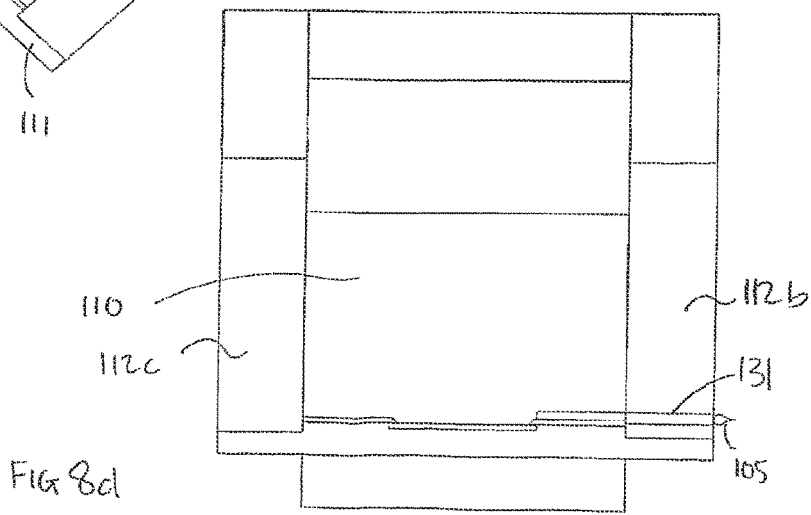

FIG. 8d shows an embodiment in which processing liquid is supplied by means of a supply means 131 arranged in a side wall of the processing apparatus, e.g. the side wall 112b of the first structure 109. It should be understood that, in embodiments, the supply through the side wall may be accomplished in an upper part, a middle part and/or a lower part of the processing apparatus.

FIG. 9 shows an embodiment of the processing apparatus comprising tubing 134, 128 connecting a liquid source 126 and a liquid waste 125 to the processing chamber 108. In the embodiment, the tubings are connected to an inlet/outlet 122 arranged at the bottom part of the processing chamber 108. The inlet/outlet 122 could be the drain 122 mentioned above.

FIG. 2 shows an optional pushing and pulling mechanism 117 for pushing and pulling the block 110 in the directions indicated by the arrow. This pushing and pulling mechanism 117 may be controlled by means of a controller to provide automatic movement of the block.

The movement of the block may be controlled mechanically by means of the pushing and pulling mechanism 117. In an alternative embodiment, the block could be arranged to float on the processing liquid applied, i.e. the block may be configured of a material selected so that the block can float on the processing liquid applied. In such an embodiment, the block could be held in position by e.g. two vertical rods that secure a one dimensional movement along the z-axis for a carrier in the x/y plane and that provides a maximum float height corresponding to said second position, i.e. of e.g. 3 mm.

In embodiments, the block is touching or very close to touching the carrier surface holding the tissue section when the block is in a processing position. Thereby, processing liquid, e.g. probe buffer or reagent, applied to the biological sample will be spread out by the close physical proximity between the block and the carrier.

In embodiments, the surface of the block spreading out the applied processing liquid is a homogenous and even surface. A pattern texture of the surface of the block may be provided. The material of the surface of the block may be Teflon™, whereby the small volume of applied processing liquid is more easily spread out over the biological sample.

In a first distance, the block will be at a distance from the carrier. In embodiments, the distance may be 1-3 mm or more. In this position process steps such as washing, heat pre-treatment, potential digestion, stringency wash and other incubation steps can be performed. The relatively short distance between the block and the carrier when the block is a second distance results in fast heating and/or cooling of the applied processing liquid to the specified temperatures in different processing steps, avoids problems with temperature gradients, and secures the use of small volumes of processing liquids.

The block can also be in a third or further distance(s), dependent on the required liquid volume for the specific processing step. This gives the apparatus according to the invention great flexibility.

An efficient mixing of liquids applied to the carrier can be obtained by repeating one or more of the x/y/z movements a number of times. Such mixing can increase the reaction rate by providing active movement of liquid components applied to the sample. It should be understood that the mixing may be a so-called chamber-mixing independent of the carrier or a carrier micro-mixing.

More than one processing liquid can also be applied to the carrier or Nock and subsequently be mixed in the apparatus. According to one embodiment the liquids can be mixed in the bottom of the chamber, i.e. not in direct contact with the sample, where after a movement of the block to a first processing position spreads the mixed liquid over the biological sample creating a thin film.

Figure 3A:
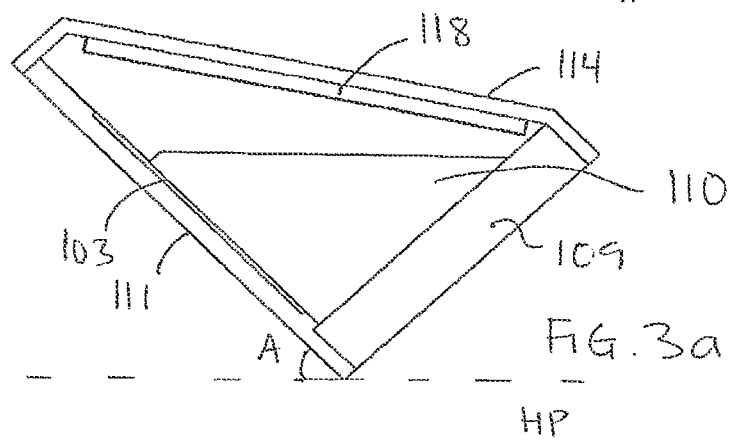
FIGS. 3a and 3b schematically show an embodiment of an apparatus for processing a biological sample, the apparatus comprising a lid.
Figure 3B:
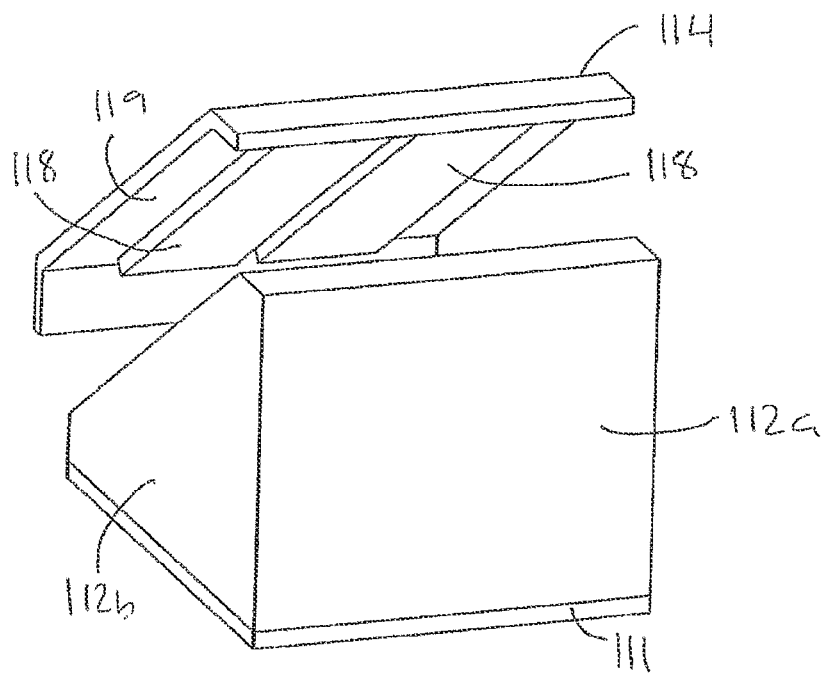

FIGS. 3a and 3b schematically illustrate an embodiment of the apparatus 100 comprising a lid 114. The lid 114 is configured to be arranged at said first structure 109 to enclose said carrier 103 and said second structure 110 during processing of said biological sample 101 arranged on said first planar surface 102.

As illustrated in FIGS. 3a and 3b, the embodiment of the apparatus 100 may comprise a reservoir 118 arranged at a surface 119 of said lid 114 that faces said second structure 110. The reservoir 118 may be to control the humidity within the processing chamber 108 during processing of said biological sample 101. The reservoir 118 may be configured as an elongated reservoir 118 comprising an absorbing material.

Humidity can also be controlled by providing a humidity reservoir, for example a reservoir in one or more of the block, platen or wall.

FIG. 10a shows an embodiment of a processing apparatus 100' for processing of two biological samples arranged on two carriers 103, 103'. As is shown in the figure, the block 110' has two planar surfaces 104, 104'. An inlet/outlet 122' is also shown.

In FIG. 10b it is shown that an amount of processing liquid 105, 105' can be applied to the planar surfaces 104, 104' of the block 110', when the block is in upper position and having the planar surfaces 104, 104' facing away from the first structure 109, 109'. In the figure it is also shown, when the block 110' is in a processing position, i.e. when the block 110' has been turned around to a position when the planar surfaces 104, 104' are facing the first structure 109, 109' and the carriers 103, 103' and when the block 110' has been inserted into the first structure 109, 109').

FIG. 11a shows a multiprocessing apparatus 129 comprising 12 processing chambers 108 having first structures 109 and blocks 110, and 12 carriers 103. The figure shows 12 blocks 110 but it should be understood that one block could be designed to cover all 12 carriers or that a block could be designed to cover a pre-determined number of carriers.

Figure 11B:
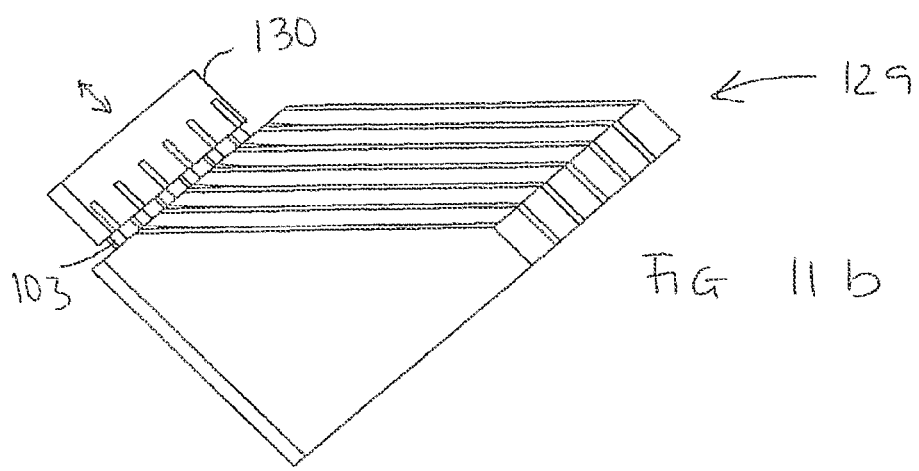
Figure 11C:
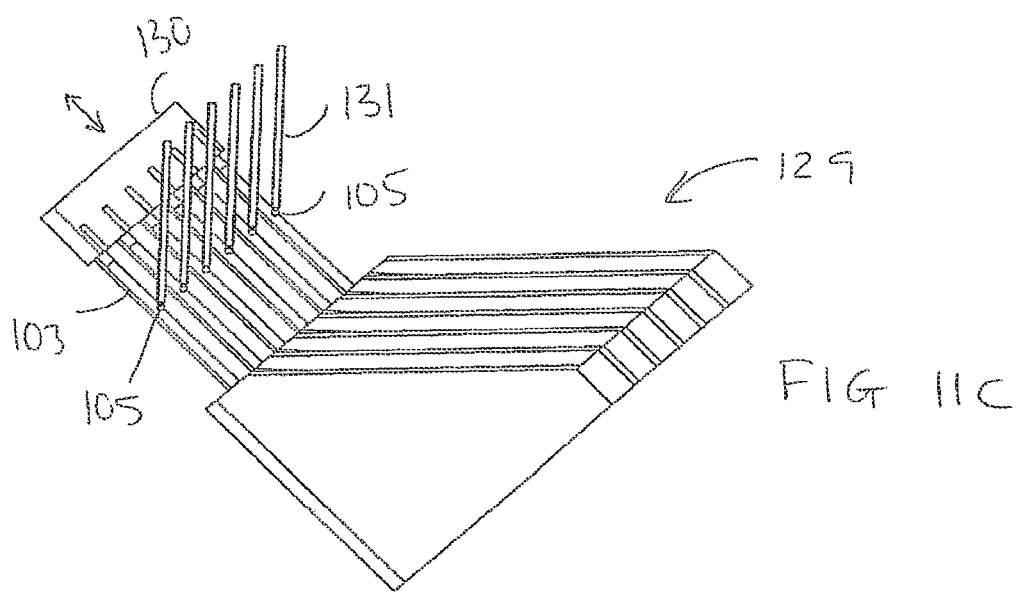

FIGS. 11b and 11c show an embodiment of a multiprocessing apparatus 129. In this embodiment, the carriers 103 are mounted on a carrier holder 130, e.g. a rack 130, whereby all the carriers 103 can be moved simultaneously. The carriers 103 may be moved in the directions of the arrow. FIG. 11c shows the supply of an amount of processing liquid 105 to each carrier 103, by means of a supply means 131 connected to a processing liquid source (not shown). In embodiments, the number of supply means 131 corresponds to the number of carriers 103, but it should be understood that one supply means could be configured to supply liquid to all of the carriers. In such embodiments, the supply means could be part of a movable robot means.

Figure 12:
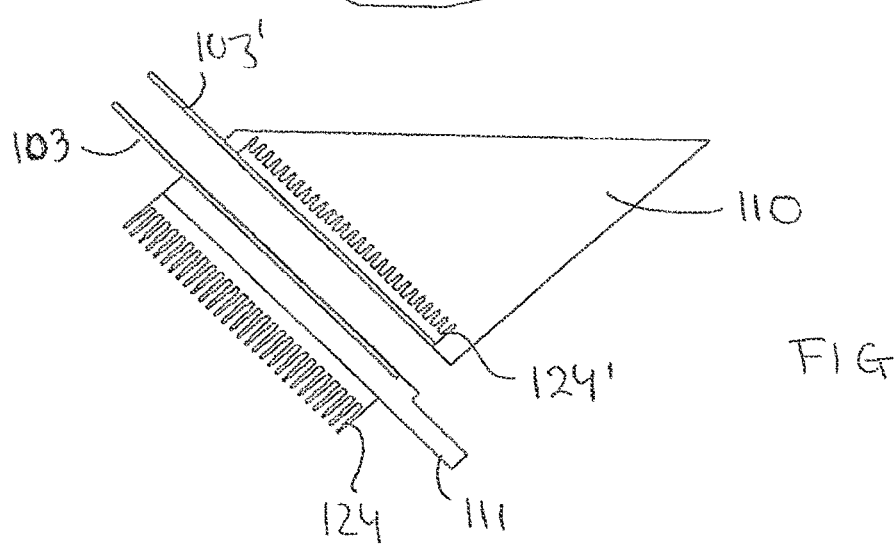
FIG. 12 schematically shows parts of an embodiment of the processing apparatus according to the invention.

FIG. 12 shows part of an embodiment of a processing apparatus for processing two biological samples arranged on carriers 103, 103'. Here the two tissue sections are facing each other and they are in contact with the same liquid during processing. This could be advantageous e.g. when one of the slides is a control slide. In other embodiments, the sample carriers comprise biological samples to be processed by the same processing liquid. In yet other embodiments, one of the sample carriers is blank, i.e. it does not contain a sample, whereby the blank sample carrier when arranged at the lower bottom plate 111 or the block 110 may serve to protect the lower bottom plate 111 or the block 110, respectively, from being contaminated with processing liquid. In the shown embodiment, the lower bottom plate 111 comprises a lower heating element 124 and the block 110 comprises an upper heating element 124'.

Figure 13:
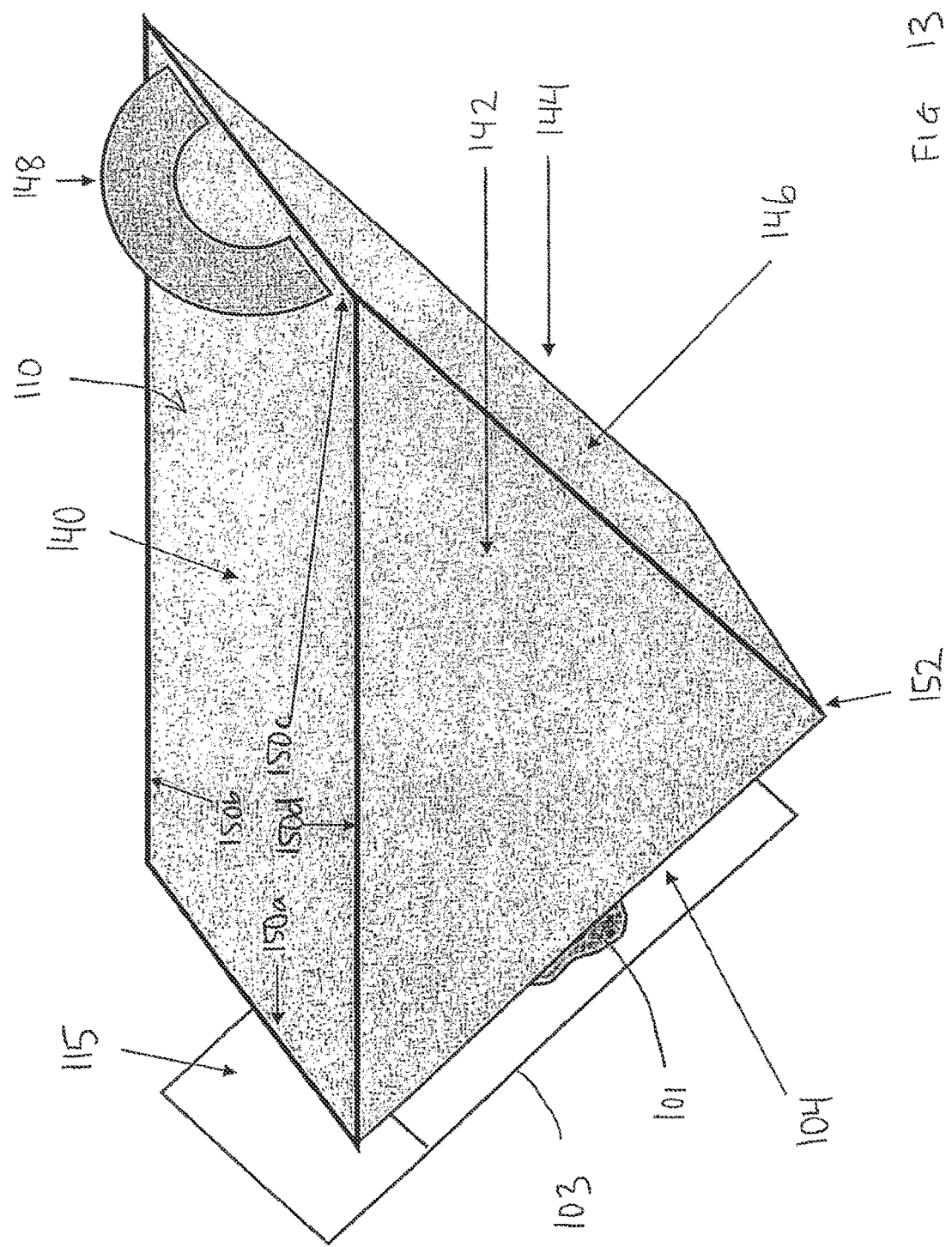
FIGS. 13-15 schematically show parts of an embodiment of the processing apparatus according to the invention.
Figure 14:
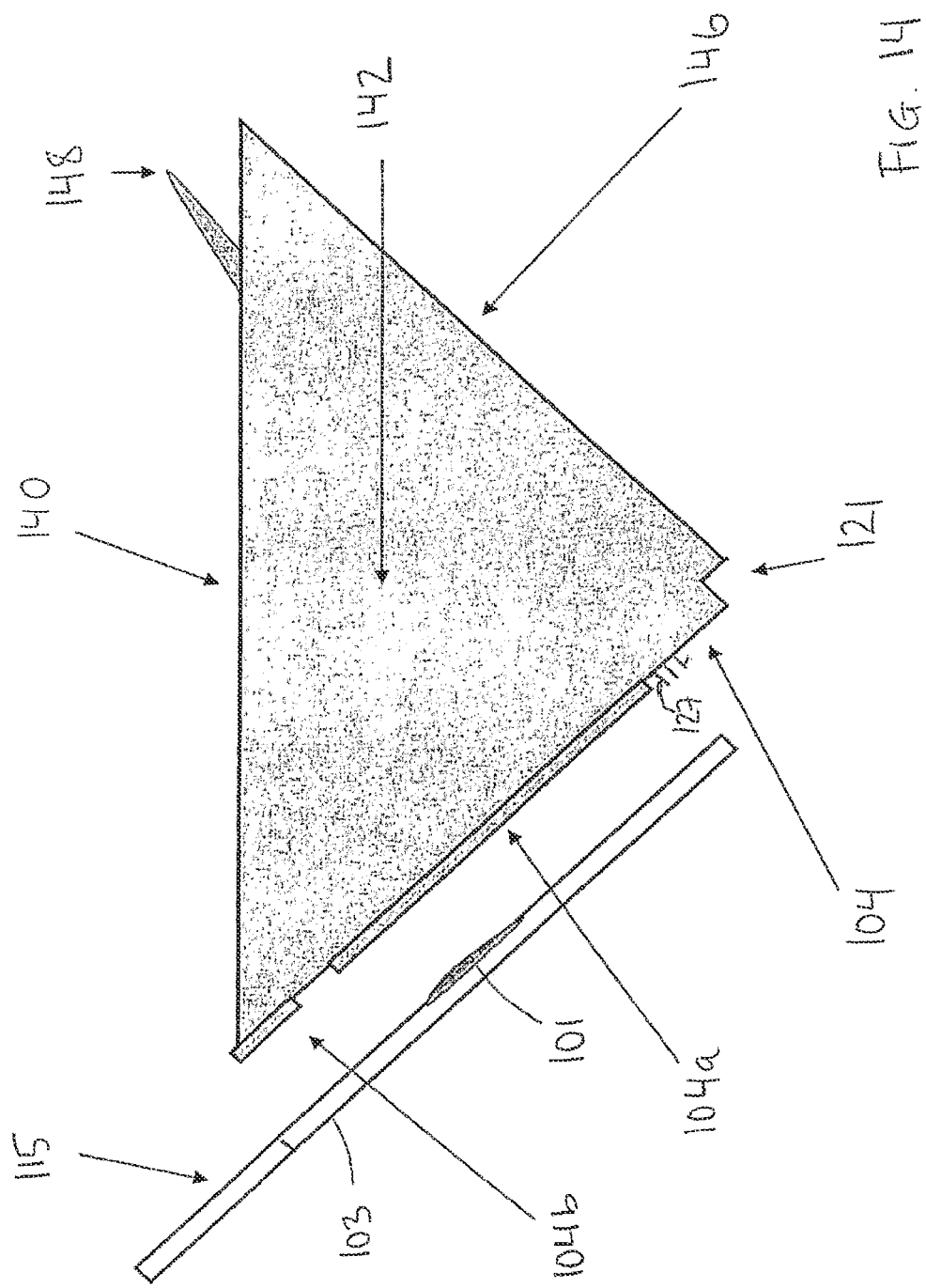
Figure 15:
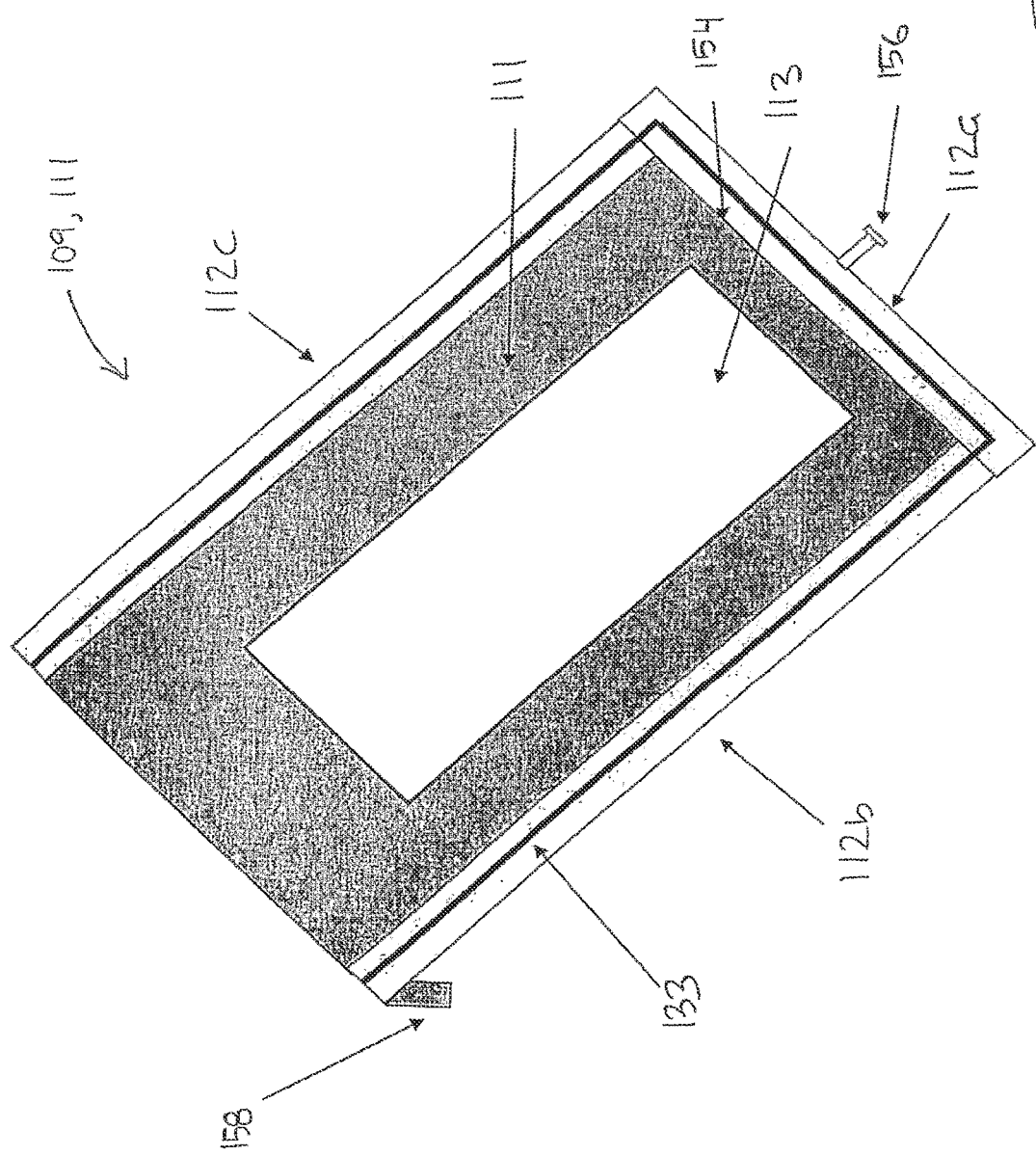

FIGS. 13-15 schematically show parts of an embodiment of the processing apparatus according to the invention.

FIG. 13 shows schematically in perspective a side view of a sample carrier 103 with a biological sample 101 and a block 110, As illustrated in the figure, the block 110 comprises a planar surface 104 also called a sample side or second planar surface, an upper side 140, a left side 142, a right side 144, a back side 146. A handle 148 may be arranged at an upper part of the block 110. The block 110 comprises further side edges 150a, 150b, 150c, 150d, and a lower edge 152.

FIG. 14 shows schematically a side view of the sample carrier 103 and block 110. As shown, the planar surface 104 comprises a planar elevation 104a arranged to cover at least a part of the sample 103. The planar surface 104 may also comprise a second elevation 104b configured to function as a sealing between the block 110 and the sample carrier 103 when the block 110 is arranged in a processing position. As illustrated in FIG. 14, the block 110 may in a lower part comprise a recess configured to provide a reservoir 121 when the block 110 is arranged in a processing position.

FIG. 15 schematically shows a cross section of the first structure 109 and the bottom plate 111. The first structure 109 comprises a back side 112a, a left side wall 112b, and a right side wall 112c. The bottom plate 111 may comprise a recess 113 configured to carry the sample carrier 103. The recess and the bottom plate may comprise an aluminium bottom. Embodiments may be provided with a sealing 133 arranged between the first structure 109 and the bottom plate 111. The sealing 133 may be a rubber strip or the like. FIG. 15 also shows a lower/bottom inner wall 154 of the processing chamber, a back screw 156 configured to secure the block at a first position and a fastening means 158 such as a hook or the like. By mean of which fastening means 158, the processing chamber may be removable fastened in the processing apparatus.

Figure 16:
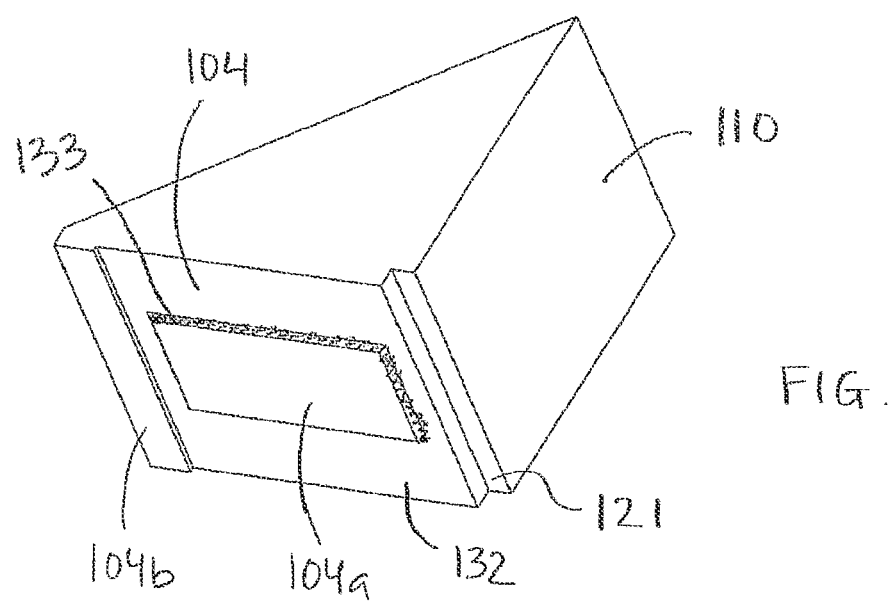
FIG. 16 schematically shows an embodiment of a block.

FIG. 16 shows an embodiment of a block 110. The block 110 comprises a second planar surface 104 comprising a planar elevation 104a arranged to cover at least a part of a biological sample 101 during processing when said second planar surface 104 is at said second distance from said first planar surface 101. The elevation 104a may have the shape of a cover glass and at least have such a shape that substantially covers the target area. The second planar surface 104 may also be provided with a second elevation 104b in a front part thereof. The second elevation 104b may be planar and may be arranged to function as a sealing or barrier.

A sealing 133 may be arranged at the outer boundary of said planar elevation 104a. The sealing 133, e.g. a rubber strip, secures that the applied amount of liquid is retained within a space defined by said sealing 133, said planar elevation 104a, and said part of said biological sample 101. Outside the space defined by the sealing 133, said planar elevation 104a, and said part of said biological sample 101 is a humidity channel to the liquid reservoir 121, whereby a relative high humidity can be provided during processing.

Figure 17:
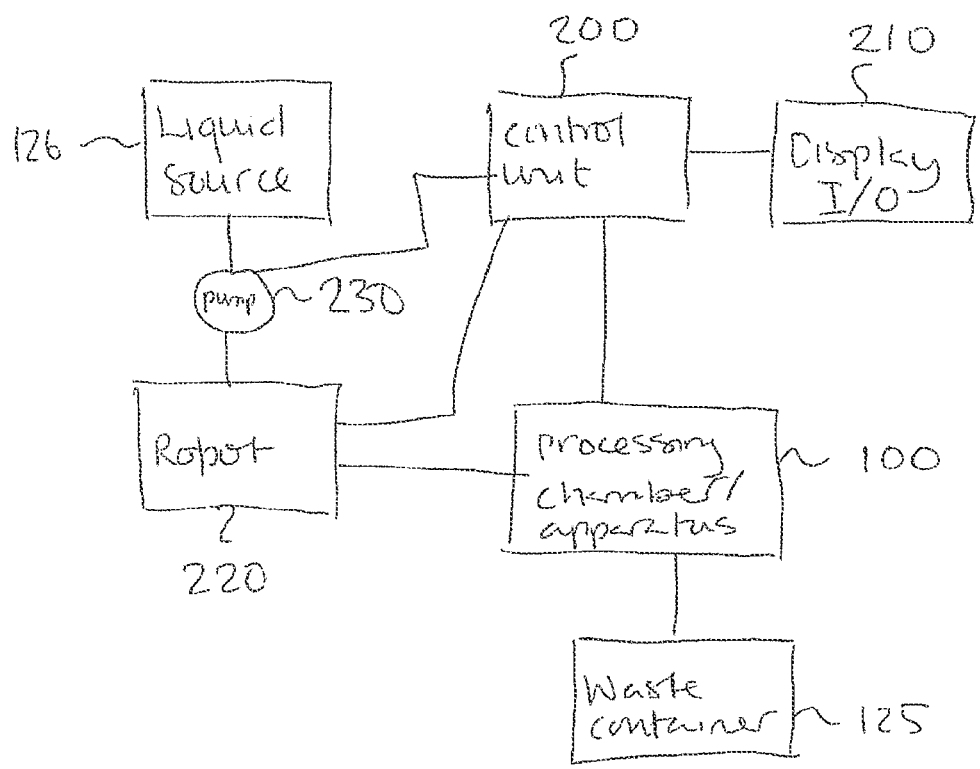
FIG. 17 schematically shows an embodiment of an inventive system.

FIG. 17 shows schematically an embodiment of an inventive system. The system comprises a processing apparatus 100. A control unit 200 may be configured to control the operation of components of the system. For example, the control unit 200 may be configured to control pumping means 230, such as a pump, and robot means 220 to supply a processing liquid from a liquid source 126. Further, the control unit controls the operation of the processing apparatus 100 and may interact with an input/output interface 210, such as a display.

Figure 18A:
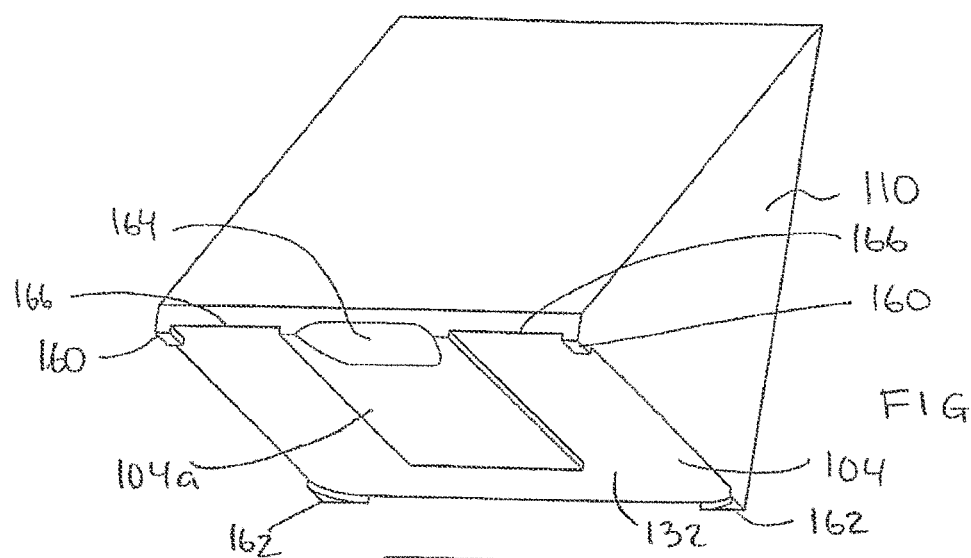
FIGS. 18a, 18b and 18c show schematically embodiments of a block.
Figure 18B:
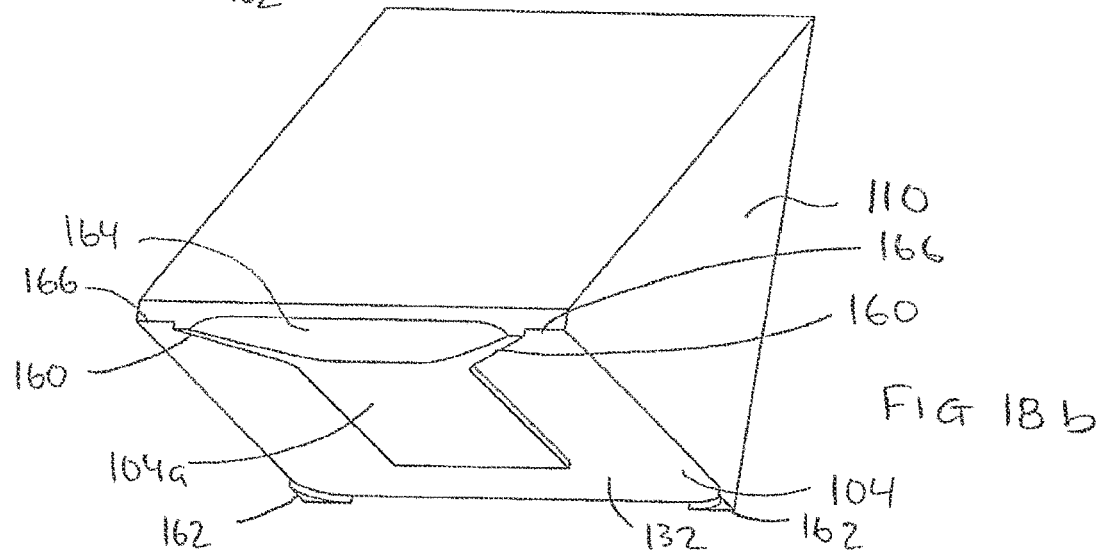
Figure 18C:
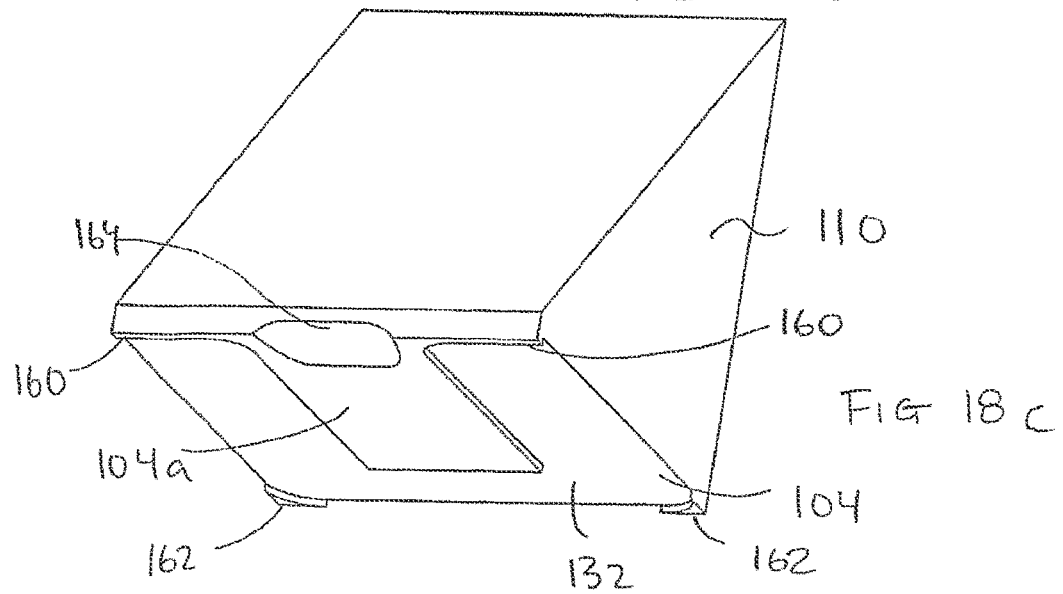

FIGS. 18a, 18b and 18c show schematically embodiments of a block 110. As illustrated, the block comprises a planar elevation 104a in the planar surface 104. Embodiments of the block may comprise a front support 160 and a back support 162 arranged to provide a humidity channel 132 around the biological sample when the block 110 is in a processing position. The supports 160, 162 may be arranged to provide a distance of e.g. 1 mm between the planar surface 104 and the sample carrier when the block is in the processing position. The supports 160, 162 can also suitably be positioned on the planar surface 104 such that, it will rest on the surface of the first planar surface, e.g. a slide.

When a block according to the embodiment shown in FIG. 18a is in a processing position, the humidity channel 132 will be open in the front part due to the recess 166 between the front supports 160 and the elevation 104a.

On the other hand, when a block according to the embodiment shown in FIG. 18c is in a processing position, the humidity channel 132 will be closed which will reduce evaporation of processing liquid. An embodiment of the block according to FIG. 18b will provide a semi-open (or semi-closed) humidity channel 132.

In a front part of the block, the block is provided with a recess 164 for supply of processing liquid. The recess 164 may have different shape and size, but should be designed to facilitate the supply of processing liquid when the block is in the processing position.

FIG. 19 schematically shows an embodiment of an apparatus for processing a biological sample according to the invention, in the embodiment the side wall 112c is removed. The block 110 in FIG. 19 corresponds to the block 110 shown in FIG. 18a, but it should be understood that the block could be of another type or have another design.

As illustrated in FIG. 19, the bottom plate 111 may be provided with a channel 168 surrounding the part of the bottom plate 111 supporting the carrier 103. As illustrated, the channel 168 may be in fluid communication with the inlet/outlet 122 by means of which inlet/outlet 122 liquid may be supplied to or withdrawn from the channel 168. Further, the channel 168 may have one or more inclined side walls 169.

It should be understood that the channel 168 may be arranged in the block 110 and/or in the bottom plate 111 as described with reference to FIG. 19.

An embodiment of the method for processing biological samples comprises the steps of:
lifting up a block of a processing chamber to an upper position;
adding an amount of a processing liquid, e.g. a probe buffer, either manually or automatically, to the biological sample to be treated. This may be done after a pre-treatment procedure;
moving the block to a processing position, whereby the applied processing liquid is distributed over the biological sample; and
processing the biological sample during a predefined time period during an optional heating and/or cooling.

Another embodiment of the method for processing biological samples comprises the steps of:
lifting up the block of a processing chamber to an upper position;
rotating the block;
adding an amount of a processing liquid, e.g. a probe buffer, either manually or automatically, to the block for further application to the biological sample. This may be done after a pre-treatment procedure;
rotating the block back;
moving the block to a processing position, whereby the applied processing liquid is distributed over the biological sample; and
processing the biological sample during a predefined time period during an optional heating and/or cooling procedure.

Another embodiment of the method for processing biological samples comprises the steps of:
lowering a block to lowermost processing position;
adding an amount of a processing liquid, e.g. a probe buffer, either manually or automatically, to the biological sample to be treated. The processing liquid is distributed by gravity and/or capillary forces. This may be done after a pre-treatment procedure; and
processing the biological sample during a predefined time period during an optional heating and/or cooling procedure.

The following is an example of IHC and FISH procedures performed using the present invention providing good results. The apparatus of the invention is used from the process steps of baking until cover slipping upon paraffin embedded tissues. The examined tissues have been fixed in neutral buffered formaldehyde from 6 to 72 hours. The tissues consist of: tonsil, liver, mamma carcinoma, medullary thyroid cancer, colon cancer, melanoma metastasis, colon, prostate, cerebellum, kidney and pancreas.

For the IHC, volumes of 10 mL were used in the deparaffination/Target Retrieval, Wash Buffer and $H_2O$ process steps. For reagents such as peroxidase, antibodies, detection system, hematoxylin volumes of 50 μL were used. The process temperature is 37° C. unless otherwise specified.

Same or similar results were obtained with volumes of 20 μL, 30 μL, 40 μL and larger.

Baking was performed at 60° C. 10 min; combined deparaffination and Target Retrieval (S1700, Dako) at 95° C. 10 min; wash (Wash Buffer 1×, S3306, Dako) for 5 min; peroxidase block (S2023, Dako) min; wash 5 min; monoclonal mouse anti-human cytokeratin (M3515, Dako) 10 min; wash 5 min; detection (K5007); rinse (Wash Buffer); wash 5 min; chromogen DAB+(K3468, Dako) 2×5 min; wash 5 min; counterstaining with Hematoxilin (S3301) for 5 min; rinse Wash Buffer; rinse with $H_2O$. The process time was about 90 minutes. Mounting was then performed in Faramount Mounting Medium (S3025, Dako).

For FISH volumes of 9 mL (brick lifted 3 mm) were used in the deparaffination/Pre-Treatment, Wash Buffer, Stringent Buffer and $H_2O$ processing steps. For the probe buffer a volume of 30 μL was used (brick 0 mm position). In baking and drying steps the brick was elevated 10 mm. The process temperature was 37° C. unless otherwise specified.

Same or similar results were obtained with volumes of 20 μL, 30 μL, 40 μL and larger.

Baking was performed at 60° C. 10 min; combined deparaffination and Target Retrieval (S1700, Dako) at 95° C. 10 min; wash (Wash Buffer 1×, S3306, Dako) for 5 min; wash 5 min (Wash Buffer 1×, K5331, Dako); Pepsin RTU (K5331, Dako) 4 min; wash 5 min (Wash Buffer 1×, K5331, Dako); wash with $H_2O$ 2 min; drying (dehydration) 5 min; 400 μL $H_2O$ to liquid reservoir; 30 μL HER2 FISH probe (K5331, Dako) at 82° C. 5 min and at 45° C. O/N (about 16 h); Stringency Wash (K5331, Dako) 65° C. 10 min; wash 5 min; wash with $H_2O$ min, drying (dehydration) 5 min. The process time until hybridization step was about 60 minutes and the process time from hybridization was stopped until mounting for about 30 min. The mounting was then performed in 15 μL Antifade Mounting Medium (K5331, Dako).

The invention claimed is:

1. An apparatus for processing a biological sample, the apparatus comprising:
a container comprising a bottom plate and at least three side walls;
a block positioned within said container, wherein said biological sample is positioned at said block and faces said bottom plate;
a liquid supply configured to supply an amount of a liquid to the biological sample;
wherein said container and said block define a processing chamber having an adjustable volume by changing a distance of the sample side surface of the block from the bottom plate of the container.

2. The apparatus of claim 1, wherein the block slopes at an angle between 0 degrees and 90 degrees with a horizontal plane on which the apparatus is disposed.

3. The apparatus of claim 1, wherein the sample side surface of the block and the bottom plate of the container are configured to be arranged substantially parallel such that a supplied amount of liquid is distributed over the sample.

4. The apparatus of claim 1, wherein the liquid supply is positioned such that the liquid is supplied from the liquid supply to flow through the processing chamber at a rate determined by gravity and capillary forces.

5. The apparatus of claim 1, further comprising an automated mixing apparatus configured to mix content within the processing chamber by moving the sample side surface relative to the bottom plate.

6. The apparatus of claim 1, further comprising a distance changing apparatus configured to change the distance between the sample side surface and the bottom plate.

7. The apparatus of claim 6, further comprising a control unit configured to control the distance changing apparatus.

8. An apparatus for processing a biological sample, said biological sample being arranged on a first planar surface of a carrier, said apparatus comprising:
 a container comprising at least three side walls and a second planar surface, said second planar surface being at a first distance from said first planar surface; and
 a liquid supply for supplying an amount of a liquid that is to be applied to said biological sample;
 wherein said first planar surface and said second planar surface are configured to be arranged substantially parallel at a second distance from each other, said second distance being different from said first distance;
 and wherein said container and said first planar surface define a processing chamber having an adjustable volume by changing a distance of said first planar surface from said second planar surface.

9. The apparatus of claim 8, wherein the second planar surface slopes at an angle between 0 degrees and 90 degrees with a horizontal plane on which the apparatus is disposed.

10. The apparatus of claim 8, wherein the bottom plate of the container is configured to be arranged substantially parallel with the first planar surface of the carrier such that a supplied amount of liquid is distributed over the sample.

11. The apparatus of claim 8, wherein the liquid supply is positioned such that the liquid is supplied from the liquid supply to flow through the processing chamber at a rate determined by gravity and capillary forces.

12. The apparatus of claim 8, further comprising an automated mixing apparatus configured to mix content within the processing chamber by moving the first planar surface relative to the second planar surface.

13. The apparatus of claim 8, further comprising a distance changing apparatus configured to change the distance between the first planar surface and the second planar surface.

14. The apparatus of claim 13, further comprising a control unit configured to control the distance changing apparatus.

15. The apparatus of claim 8, wherein the carrier is a slide having a tissue sample thereon.

16. The apparatus of claim 8, wherein the bottom plate comprises an elevation for supporting the carrier.

17. A method for processing a biological sample, comprising:
 providing a container comprising a bottom plate and at least three side walls;
 positioning a block within the container such that a sample side surface of the block is arranged substantially parallel to the bottom plate of the container, wherein a processing chamber is defined between the container and the block;
 supplying an amount of a liquid to the biological sample; and
 changing a distance between the first planar surface and the second planar surface so as to change the volume of the processing chamber.

18. The method of claim 17, wherein the bottom plate forms an angle between 0 degrees and 90 degrees with a horizontal plane on which the container is disposed.

19. The method of claim 17, wherein supplying the amount of the liquid to the biological sample comprises releasing the liquid such that the liquid is supplied from a liquid supply to flow through the processing chamber at a rate determined by gravity and capillary forces.

20. The method of claim 17, further comprising mixing the liquid within the processing chamber by moving the sample side surface relative to the container.

21. A method for processing a biological sample comprising:
 providing a container comprising at least three side walls and a second planar surface, said second planar surface being at a first distance from a first planar surface of a carrier comprising said biological sample; and
 supplying an amount of a liquid that is to be applied to said biological sample;
 changing a distance between said first planar surface and said second planar surface so as to change the volume of a processing chamber defined by said container and said first planar surface.

22. The method of claim 21, wherein supplying the amount of the liquid to the biological sample comprises releasing the liquid such that the liquid is supplied from a liquid supply to flow through the processing chamber at a rate determined by gravity and capillary forces.

23. The method of claim 21, further comprising mixing the liquid within the processing chamber by moving the sample side surface relative to the container.

* * * * *